US009187493B2

(12) United States Patent
Takimiya et al.

(10) Patent No.: US 9,187,493 B2
(45) Date of Patent: Nov. 17, 2015

(54) HETEROCYCLIC COMPOUND AND USE THEREOF

(71) Applicants: Kyushu University, National University Corporation, Fukuoka (JP); Nippon Kayaku Kabushiki Kaisha, Tokyo (JP)

(72) Inventors: Kazuo Takimiya, Higashihiroshima (JP); Chihaya Adachi, Fukuoka (JP); Masaaki Ikeda, Tokyo (JP)

(73) Assignee: Nippon Kayaku Kabushiki Kaisha, Tokyo (JP)

( * ) Notice: Subject to any disclaimer, the term of this patent is extended or adjusted under 35 U.S.C. 154(b) by 0 days.

(21) Appl. No.: 14/421,294

(22) PCT Filed: Aug. 5, 2013

(86) PCT No.: PCT/JP2013/071120
§ 371 (c)(1),
(2) Date: Feb. 12, 2015

(87) PCT Pub. No.: WO2014/027581
PCT Pub. Date: Feb. 20, 2014

(65) Prior Publication Data

US 2015/0218185 A1 Aug. 6, 2015

(30) Foreign Application Priority Data

Aug. 14, 2012 (JP) ................................ 2012-179837

(51) Int. Cl.
*C07D 495/22* (2006.01)
*H01L 51/00* (2006.01)
*H01L 51/05* (2006.01)

(52) U.S. Cl.
CPC .......... *C07D 495/22* (2013.01); *H01L 51/0074* (2013.01); *H01L 51/0512* (2013.01)

(58) Field of Classification Search
CPC .................................................... C07D 495/22
USPC ........................................................... 549/41
See application file for complete search history.

(56) References Cited

U.S. PATENT DOCUMENTS

| | | | |
|---|---|---|---|
| 3,278,552 | A | 10/1966 | Geering |
| 3,433,874 | A | 3/1969 | Geering |
| 2009/0001357 | A1 | 1/2009 | Takimiya et al. |
| 2009/0261300 | A1 | 10/2009 | Watanabe |
| 2010/0032655 | A1 | 2/2010 | Takimiya et al. |
| 2010/0065826 | A1 | 3/2010 | Takimiya et al. |
| 2011/0040107 | A1 | 2/2011 | Goto et al. |
| 2011/0250719 | A1 | 10/2011 | Zuberi et al. |
| 2011/0303910 | A1 | 12/2011 | Kuwabara et al. |
| 2012/0161109 | A1 | 6/2012 | Wigglesworth et al. |
| 2014/0051865 | A1 | 2/2014 | Takimiya |

FOREIGN PATENT DOCUMENTS

| | | | |
|---|---|---|---|
| EP | 1847544 | A1 | 10/2007 |
| EP | 2067782 | A1 | 6/2009 |
| EP | 2077590 | A1 | 7/2009 |
| EP | 2098527 | A1 | 9/2009 |
| EP | 2368892 | A1 | 9/2011 |
| GB | 2465626 | A | 6/2010 |
| JP | 2005-154371 | A | 6/2005 |
| JP | 2008-239987 | A | 10/2008 |
| JP | 2008-290963 | A | 12/2008 |
| JP | 2010-202523 | A | 9/2010 |
| JP | 2010-254599 | A | 11/2010 |
| JP | 2010-275192 | A | 12/2010 |
| JP | 2011-256144 | A | 12/2011 |
| JP | 2012-1442 | A | 1/2012 |
| JP | 2012-510454 | A | 5/2012 |
| JP | 2012-134482 | A | 7/2012 |

(Continued)

OTHER PUBLICATIONS

International Search Report mailed Oct. 1, 2013 in corresponding PCT application No. PCT/JP2013/071120.
Written Opinion mailed Oct. 1, 2013 in corresponding PCT application No. PCT/JP2013/071120.
International Preliminary Report on Patentability mailed Feb. 26, 2015 in corresponding PCT application No. PCT/JP2013/071120.
International Search Report mailed Sep. 24, 2013 in co-pending PCT application No. PCT/JP2013/072417.
Written Opinion mailed Sep. 24, 2013 in co-pending PCT application No. PCT/JP2013/072417.
International Preliminary Report on Patentability mailed Mar. 5, 2015 in co-pending PCT application No. PCT/JP2013/072417.

(Continued)

*Primary Examiner* — Taofiq A Solola
(74) *Attorney, Agent, or Firm* — Nields, Lemack & Frame, LLC

(57) ABSTRACT

Provided is a novel compound that can be applied to an organic electronics element. More specifically, provided is a novel heterocyclic compound applicable to organic electronics elements such as an organic EL element, an organic solar cell element, an organic transistorelement and an organic semiconductor laser element. The compound is a heterocyclic compound represented by the following general formula (1):

(1)

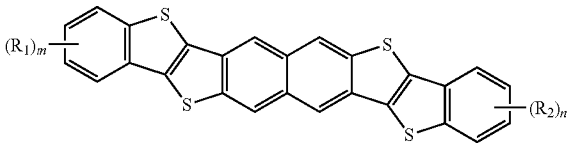

wherein $R_1$ and $R_2$ independently represent a hydrogen atom, an aryl group that may have a substituent or an alkyl group that may have a substituent; m and n independently represent an integer of 1 to 4; and when $R_1$ and $R_2$ are two or more, one of $R_1$'s and one of $R_2$'s may be each the same as or different from one another.

10 Claims, 4 Drawing Sheets

(56) References Cited

FOREIGN PATENT DOCUMENTS

| | | | |
|---|---|---|---|
| SU | 755785 | A1 | 8/1980 |
| WO | 2006/077888 | A1 | 7/2006 |
| WO | 2008/026602 | A1 | 3/2008 |
| WO | 2008/047896 | A1 | 4/2008 |
| WO | 2008/050726 | A1 | 5/2008 |
| WO | 2009/128559 | A1 | 10/2009 |
| WO | 2010/058692 | A1 | 5/2010 |
| WO | 2010/098372 | A1 | 9/2010 |
| WO | 2012/010292 | A1 | 1/2012 |

OTHER PUBLICATIONS

J. Am. Chem. Soc., 2007, vol. 129, pp. 15732-15733, "Highly Soluble [1]Benzothieno[3,2-b]benzothiophene (BTBT) Derivatives for High-Performance, Solution-Processed Organic Field-Effect Transistors", Ebata, et al.

Advanced Materials, 2009, vol. 21, pp. 213-216, "Dithieno[2,3-d;2'3'-d']benzo[1,2-b;4,5-b']dithiophene (DTBDT) as Semiconductor for High-Performance, Solution-Processed Organic Field-Effect Transistors", Gao, et al.

J. Org. Chem, 2005, vol. 70, pp. 1147-1153, "Synthesis and Structural, Electronic, and Optical Properties of Oligo (thienylfuran)s in Comparison with Oligothiophenes and Oligofurans", Miyata, et al.

J. Heterocyclic Chem., May-Jun. 1998, vol. 35(3), pp. 725-726, "A Simple One-Pot Synthesis of [1]Benzotelluro[3,2-b] [1]-benzotellurophenes and its Selenium and Sulfur Analogues from 2,2'-Dibromodiphenylacetylene [1]", Sashida, et al.

J. Am. Chem. Soc., 2011, vol. 133, pp. 5024-5035, "Linear- and Angular-Shaped Naphthodithiophenes: Selective Synthesis, Properties, and Application to Organic Field-Effect Transistors", Shinamura, et al.

J. Am. Chem. Soc., 2004, vol. 126, pp. 5084-5085, "2,6-Diphenylbenzo[1,2-b:4,5-b']dichalcogenophenes: A New Class of High-Performance Semiconductors for Organic Field-Effect Transistors", Takimiya, et al.

J. Am. Chem. Soc., 2006, vol. 128, pp. 12604-12605, "2,7-Diphenyl[1]benzothieno[3,2-b]benzothiophene, A New Organic Semiconductor for Air-Stable Organic Field-Effect Transistors with Mobilities up to 2.0 cm2 V-1 s-1", Takimiya, et al.

Science and Technology of Advanced Materials, 2007, vol. 8(4), pp. 273-276, "Design strategy for air-stable organic semiconductors applicable to high-performace field-effect transistors", Takimiya, et al.

J. Am. Chem. Soc., 2007, vol. 129, pp. 2224-2225, "Facile Synthesis of Highly Pi-Extended Heteroarenes, Dinaphtho [2,3-b"2',3'-f]chalcogenopheno[3,2-b]chalcogenophenes, and Their Application to Field-Effect Transistors", Yamamoto, et al.

J. Org. Chem., 2002, vol. 67, pp. 1905-1909, "Synthesis of 2,3-Disubstituted Benzo[b]thiophenes via Palladium-Catalyzed Coupling and Electrophilic Cyclization of Terminal Acetylenes", Yue, et al.

J. Org. Chem., 2005, vol. 70, pp. 10292-10296, "Synthesis of 2,3-Disubstituted Benzo[b]furans by the Palladium-Catalyzed Coupling of o-lodoanisoles and Terminal Alkynes, Followed by Electrophilic Cyclization", Yue, et al.

Office Action mailed Aug. 14, 2014 in co-pending U.S. Appl. No. 14/423,516.

European communication dated Aug. 20, 2015 in co-pending European patent application No. EP 13830648.5.

"Aryl-Aryl Bond Formation by Transition-Metal-Catalyzed Direct Arylation", Dino Alberico et al., Chemical Reviews, vol. 107, No. 1, pp. 174-238, Jan. 2007.

HETEROCYCLIC COMPOUND AND USE THEREOF

TECHNICAL FIELD

The present invention relates to a novel heterocyclic compound and use thereof More specifically, the present invention relates to a specific organic compound and an organic electronics device comprising the same.

BACKGROUND ART

Recently, organic electronics devices have drawn increasing attention. The devices are characterized by flexibility, applicability to a large area, and feacibility of employing a low-cost and high-speed printing process in manufacturing electronics devices. Typical devices include an organic EL element, an organic solar cell element, an organic photoelectric conversion element and an organic transistor element. An organic EL element is expected to be a main target for a flat panel display in the next-generation display and has been applied to displays of mobile phones through TV sets and the like. The development of organic EL elements has been continued toward further higher functionalization. Organic solar cell elements and the like have been researched and developed for a flexible and inexpensive energy source. Organic transistor elements and the like have been researched and developed to be applied to flexible displays and low-cost ICs.

To develop these organic electronics devices, it is very important to develop semiconductor materials constituting the devices. Acene organic semiconductors such as pentacene, which is a low molecular weight semiconductor material, have been aggressively investigated for an organic transistor material. Regarding heterocyclic compounds, hetero acene compounds, in particular, containing a sulfur or selenium atom, have been mainly investigated, and benzodithiophene (DPh-BDT), naphthodithiophene (NDT), benzothienobenzothiophene (DPh-BTBT, AlkylBTBT) and dinaphthodithiophene (DNTT) have been developed for materials stable in the air and having high performance (Patent Literatures 1-5, Non Patent Literatures 1-5). These compounds have more excellent semiconductor properties and higher stability as compared to pentacene, but the performance of these compounds appears to be still insufficient. In fact, these compounds have not been commercially exploited. In the circumstance, it is still important to develop a semiconductor material having a high carrier mobility and high stability (i.e., high heat resistance and high weather resistance) and useful for various devices.

CITATION LIST

Patent Literature

Patent Literature 1: JP 2005-154371 A

Patent Literature 2: WO2010/058692

Patent Literature 3: WO2006/077888

Patent Literature 4: WO2008/047896

Patent Literature 5: WO2008/050726

Non Patent Literature

Non Patent Literature 1: J. Am. Chem. Soc., 2004, 126, 5084

Non Patent Literature 2: J. Am. Chem. Soc., 2006, 128, 12604

Non Patent Literature 3: J. Am. Chem. Soc., 2007, 129, 15732

Non Patent Literature 4: J. Am. Chem. Soc., 2011, 133, 5024

Non Patent Literature 5: J. Am. Chem. Soc., 2007, 129, 2224

SUMMARY OF INVENTION

Technical Problem

An object of the present invention is to provide a novel compound that can be applied to an organic electronics device. More specifically, a heterocyclic compound applicable to organic electronics devices such as an organic EL device, an organic solar cell device, an organic transistor device and an organic semiconductor laser device and represented by the following formula (1).

Solution to Problem

The present inventors developed a novel heterocyclic derivative with a view to solving the aforementioned problem and assessed possibility as an organic electronics device, thereby achieving the present invention.

More specifically, the present invention is as follows:

[1] A heterocyclic compound represented by the general formula (1):

[Formula 1]

(1)

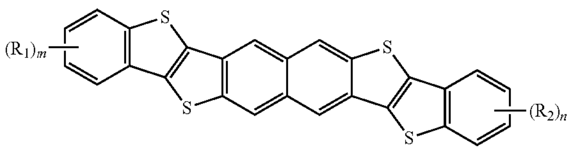

wherein $R_1$ and $R_2$ independently represent a hydrogen atom, an aryl group that may have a substituent or an alkyl group that may have a substituent; m and n independently represent an integer of 1 to 4; and when $R_1$ and $R_2$ each are two or more, one of $R_1$'s and one of $R_2$'s may be each the same as or different from one another.

[2] The heterocyclic compound according to [1], wherein $R_1$ and $R_2$ are each a hydrogen atom or an alkyl group that may have a substituent.

[3] The heterocyclic compound according to [2], wherein $R_1$ and $R_2$ each are a hydrogen atom or a C1 to C3 lower alkyl group.

[4] The heterocyclic compound according to [3], wherein $R_1$ and $R_2$ each are a hydrogen atom.

[5] An organic semiconductor material containing the compound according to any one of [1] to [4].

[6] A thin film comprising the organic semiconductor material according to [5]

[7] An organic electronics device comprising the organic semiconductor material according to [5].

[8] The organic electronics device according to [7], wherein the organic electronics device is a thin-film transistor element, a photoelectric conversion element, an organic solar cell, an organic EL element, an organic light emitting transistor element or an organic semiconductor laser element.

[9] The organic electronics device according to [8], wherein the organic electronics device is a thin-film transistor element, a photoelectric conversion element or an organic solar cell.

[10] The organic electronics device according to [8], wherein the organic electronics device is a thin-film transistor element.

Advantageous effects of Invention

The present invention relates to a novel compound and an organic electronics device comprising the same. The compound has satisfactory semiconductor properties and further has stability (e.g., heat resistance, weather resistance). The compound can be therefore used to provide organic electronics devices having excellent characteristics. The compound would also allow flexible electronic products to be provided.

DESCRIPTION OF EMBODIMENTS

Figure 1:
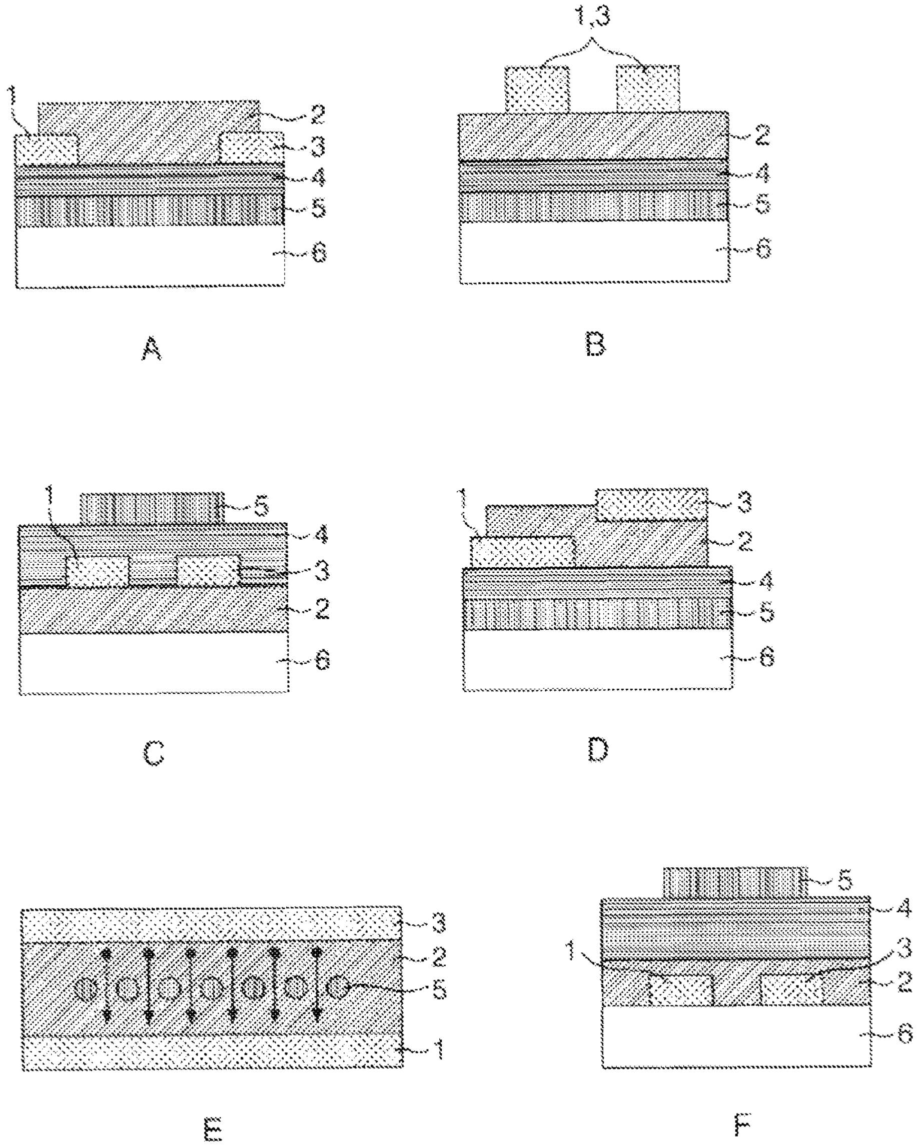
FIG. 1 is a schematic view showing the thin-film transistors according embodiments of the present invention.

Hereinafter, the present invention will be described in more detail.

A heterocyclic compound represented by formula (1) will be described.

[Formula 2]

(1)

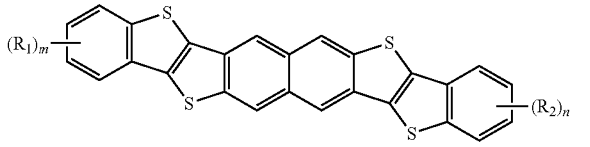

In the formula, $R_1$ and $R_2$ independently represent a hydrogen atom, an aryl group that may have a substituent or an alkyl group that may have a substituent. The positions, number and type of substituents $R_1$ and $R_2$ are not particularly defined, but the number of the substituents may fall within the range of 0 to 8 per heterocyclic compound represented by the general formula (1). In the formula (1), the numbers of $R_1$ and $R_2$ are represented by m and n, respectively; and m and n each independently represent an integer of 0 to 4 (0, 1, 2, 3 or 4). When $R_1$ and $R_2$ are each two or more, at least two types of substituents may be co-present and one of $R_1$'s and one of $R_2$'s may be the same as or different from one another.

Examples of the aryl group as mentioned above include an aromatic hydrocarbon group such as a phenyl group, a naphthyl group, an anthryl group, a phenanthryl group, a pyrenyl group and a benzopyrenyl group; a heterocyclic group such as a pyridyl group, a pyrazyl group, a pyrimidyl group, a quinolyl group, an isoquinolyl group, a pyrrolyl group, an indolenyl group, an imidazolyl group, a carbazolyl group, a thienyl group, a furyl group, a pyranyl group and a pyridonyl group; and a condensed heterocyclic group such as a benzoquinolyl group, an anthraquinolyl group, a benzothienyl group and a benzofuryl group. Among them, a phenyl group, a naphthyl group, a pyridyl group and a thienyl group are preferable, and a phenyl group is particularly preferable.

Examples of the alkyl group as mentioned above include a saturated or unsaturated and linear, branched or cyclic alkyl group preferably having 1 to 20 carbon atoms. Examples of the saturated or unsaturated and linear or branched alkyl group include a methyl group, an ethyl group, an n-propyl group, an iso-propyl group, an n-butyl group, an iso-butyl group, an allyl group, a t-butyl group, an n-pentyl group, an n-hexyl group, an n-octyl group, an n-decyl group, an n-dodecyl group, an n-stearyl group and an n-butenyl group. Examples of the cyclic alkyl group include a cycloalkyl group having 3 to 12 carbon atoms, such as a cyclohexyl group, a cyclopentyl group, an adamantyl group and a norbornyl group. A saturated linear alkyl group is preferable, and a C1-3 lower alkyl group is particularly preferable.

Examples of the substituent, which the aryl group or the alkyl group may have, include, but not particularly limited to, an aryl group, a halogen atom and an alkyl group. Examples of an aryl group and an alkyl group as a substituent may be the same as those of the aryl group and the alkyl group defined in Rs. Examples of the halogen atom include a fluorine atom, a chlorine atom, a bromine atom and an iodine atom. Among them, a C1 to C3 lower alkyl group is preferable. The number of substituents that Rs, i.e., the aryl group and the alkyl group, may have is not particularly limited.

A heterocyclic compound represented by the general formula (1) can be obtained, for example, through the following reaction process. Herein, in order to facilitate understanding, $(R_1)_m$, $(R_2)_n$ are collectively represented by R. An intermediate compound represented by the formula (2) (see Patent Literature 2) is reacted with a tin compound to obtain an intermediate compound represented by the formula (3). Further, Stille coupling reaction of the intermediate compound with a halogenated benzene derivative represented by formula (4) is performed to synthesize a prering-closed compound represented by formula (5). Intramolecular cyclization and demethylation reaction are performed to obtain a desired heterocyclic compound represented by the general formula (1).

[Formula 3]

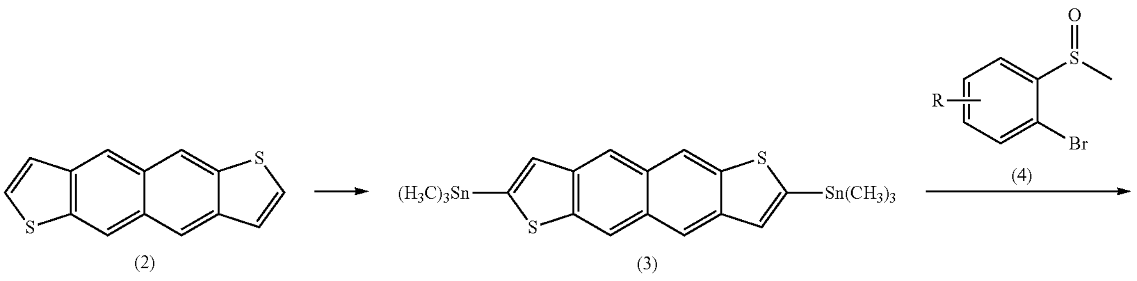

-continued

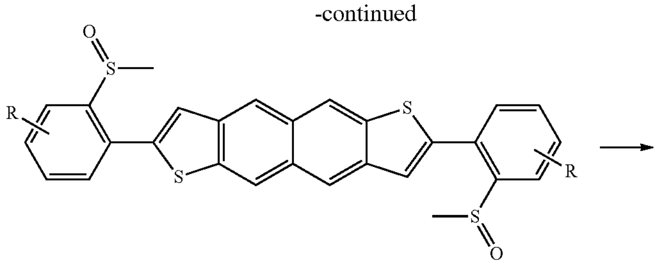

(5)

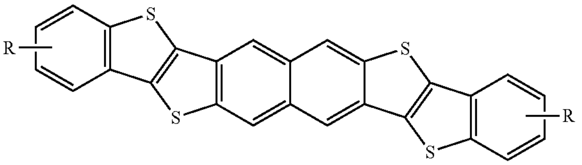

(1)

A method for purifying a compound represented by the general formula (1) is not particularly limited, and a known method such as recrystallization, column chromatography and vacuum sublimation purification can be employed. If necessary, these methods may be employed in combination.

Specific examples of a compound represented by the general formula (1) are set forth below, but the present invention is not limited to them.

[Formula 4]

(10)

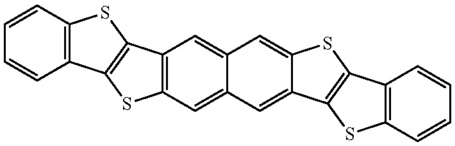

(11)

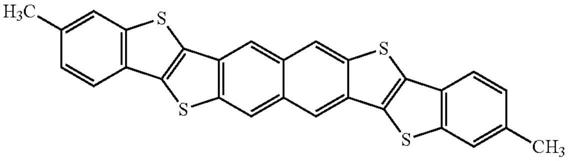

(12)

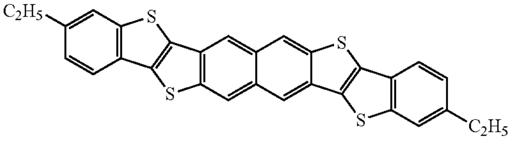

(13)

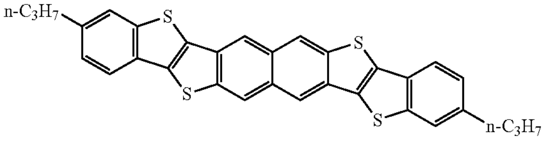

(14)

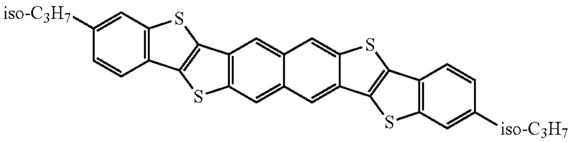

(15)

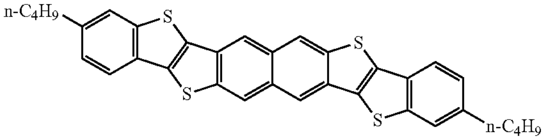

(16)

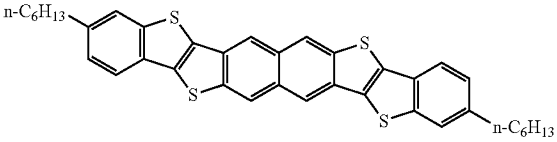

(17)

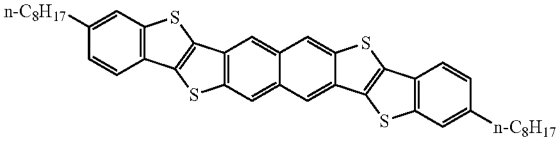

-continued
(18)
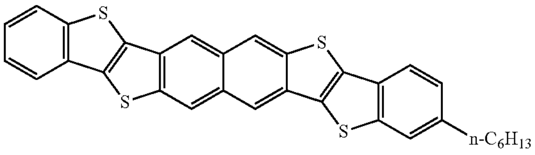
(19)
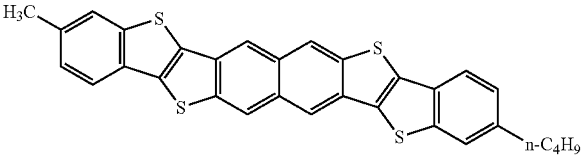
[Formula 5]
(20)
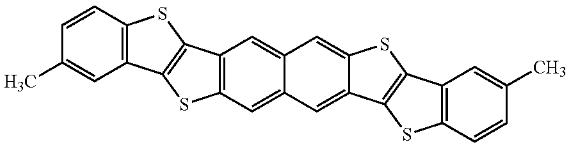
(21)
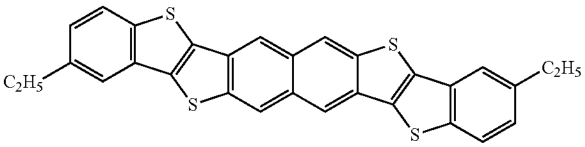
(22)
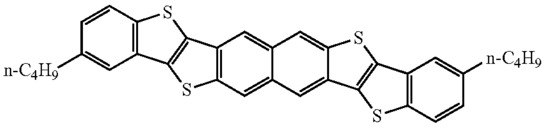
(23)
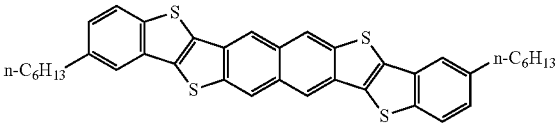
(24)
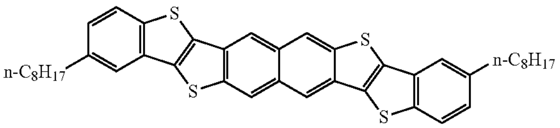
(25)
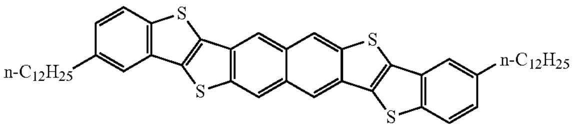
(26)
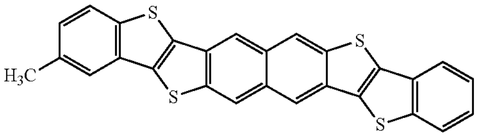
(27)
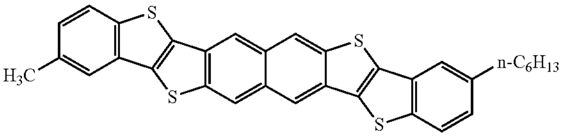
(28)
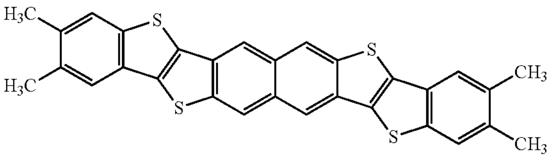
(29)
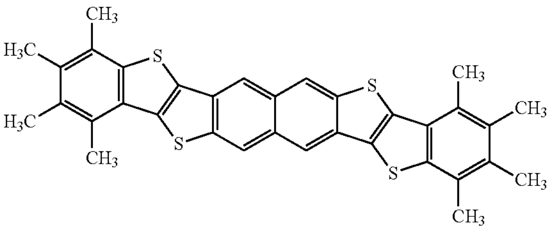
(30)
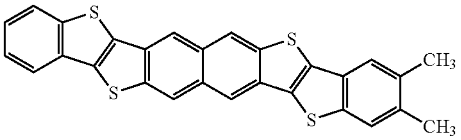
(31)
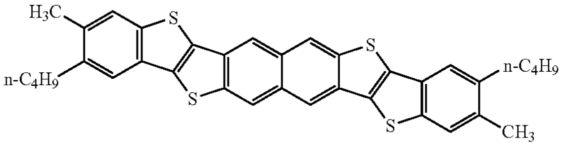

-continued
[Formula 6]
(32)
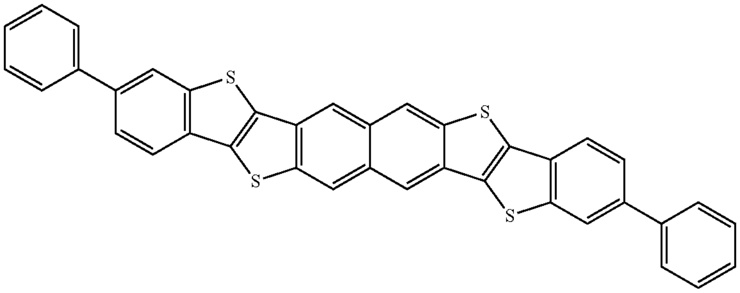
(33)
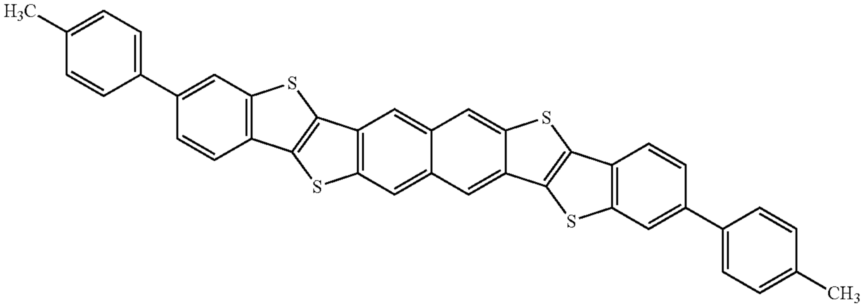
(34)
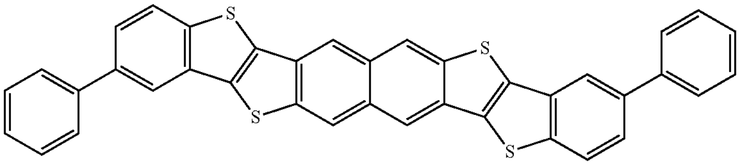
(35)
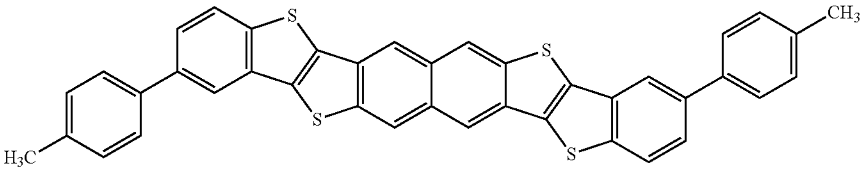
(36)
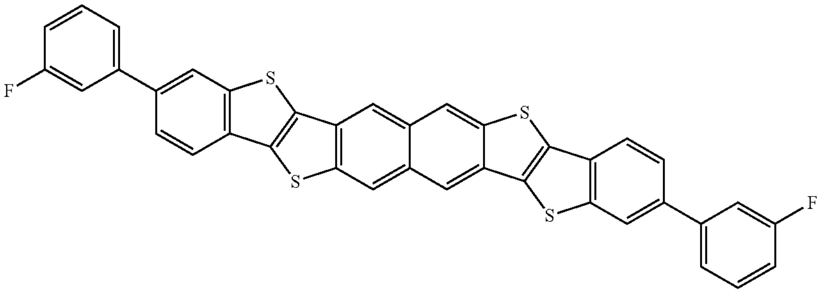
(37)
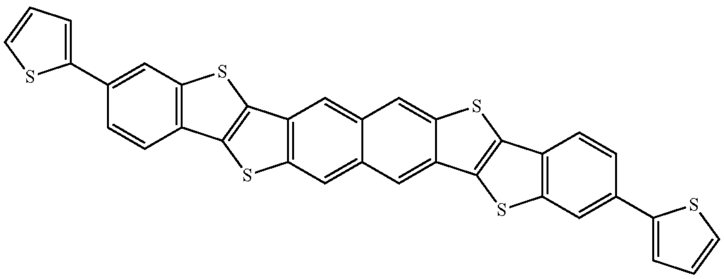

-continued (38)

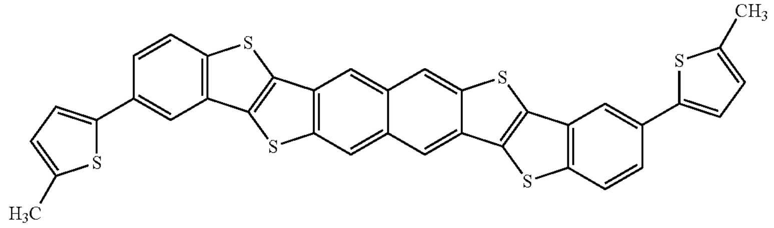

(39)

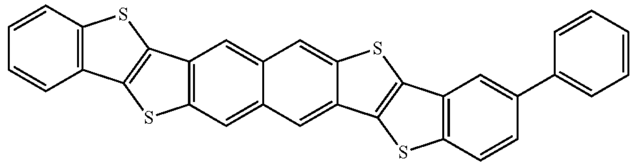

(40)

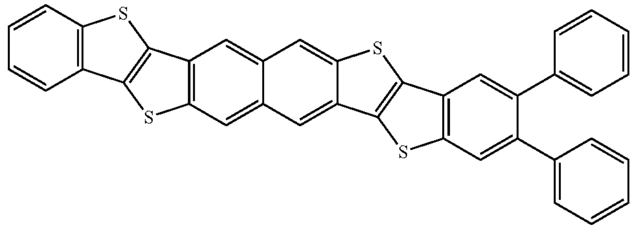

(41)

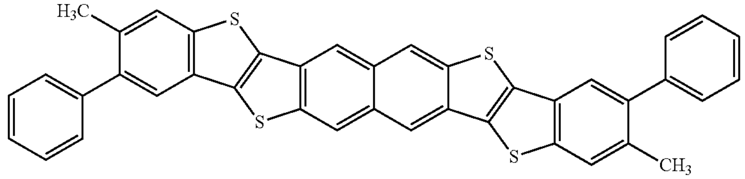

A thin film can be formed from an organic semiconductor material containing a heterocyclic compound represented by the general formula (1) of the present invention. The film thickness of a thin film varies depending upon its applications, but it is usually 0.1 nm to 10 μm, preferably 0.5 nm to 3 μm and more preferably 1 nm to 1 μm.

Examples of a method for forming a thin film generally include a vacuum process such as a resistance heating vapor deposition, an electron beam vapor deposition, a sputtering and a molecular stacking method; a solution process such as a spin coating method, a drop casting method, a dip coating method and a spray method; a relief printing method such as a flexo printing and a resin relief printing; a flat-plate printing method such as an offset printing method, a dry offset printing method, and a pad printing method; an intaglio printing method such as a gravure printing method; a screen printing method such as a silk screen printing method, a mimeographic printing method and a lithograph printing method; an inkjet printing method; a micro contact print method; and a combination of two or more thereof Among them, a resistance heating vapor deposition method, which is a vacuum process, is preferable.

A heterocyclic compound represented by the general formula (1) can be employed as an electronics material. For example, an organic electronics device can be manufactured from the compound. Examples of the organic electronics device include a thin-film transistor, a photoelectric conversion element, an organic solar cell element, an organic EL element, an organic light emitting transistor element and an organic semiconductor laser element. These will be more specifically described.

First, a thin-film transistor will be specifically described.

A thin-film transistor may have two electrodes (i.e., a source electrode and a drain electrode) in contact with a semiconductor. The current flowing between the electrodes is controlled by voltage applied to another electrode called a gate electrode.

Generally, the thin-film transistor device may frequently have a MIS (Metal-Insulator-Semiconductor) structure where a gate electrode is insulated by an insulating film. The structure where a metal oxide film is used as the insulating film is called a MOS structure. Besides these, there is a structure where a gate electrode is formed via the Schottky barrier (i.e., MES structure), but a thin-film transistor containing an organic semiconductor material may frequently have a MIS structure.

Hereinafter, referring to the drawings, the organic thin-film transistor will be more specifically described, but the present invention is not limited to these structures.

FIG. 1 shows some embodiments of the thin-film transistor (element).

In each of the embodiments shown in FIG. 1, reference numeral 1 represents a source electrode, 2 a semiconductor layer, 3 a drain electrode, 4 an insulating layer, 5 a gate electrode and 6 a substrate, respectively. The arrangement of individual layers and electrodes can be appropriately selected depending upon applications of the element. A to D, and F are called a horizontal transistor because current flows in a direction parallel to the substrate. A is called as a bottom-contact bottom-gate structure, and B is called as a top-contact bottom-gate structure. C is called as a top-contact top-gate structure where source and drain electrodes and an insulating layer are provided on a semiconductor and a gate electrode is formed thereon. D is a structure called a top & bottom-contact bottom-gate type transistor. F is a bottom-contact top-gate structure. E shows a schematic view of a transistor having a vertical structure, that is, a static induction transistor (SIT). In the SIT, current flow spreads in a plane, a large amount of carriers can move at a time. A source electrode and a drain electrode are arranged vertically, and the distance between the electrodes can be therefore reduced. As a result, a response is made at a high speed. Accordingly, a SIT can be preferably employed to supply a large amount of current and to switch at a high speed. In FIG. 1E, a substrate is not shown, but a substrate is usually provided outside the source or drain electrodes represented by reference numerals 1 and 3, respectively, in FIG. 1E.

Individual constituent elements in each embodiment will be described.

It is necessary for a substrate 6 to hold the layers to be formed thereon without being removed. A substrate may be from an insulating material such as a resin plate or film, paper, glass, quartz and ceramic; an insulating layer coated on a conductive substrate may be from a metal, an alloy or the like; or a composite material of a resin and an inorganic material in various combinations. A resin film may be from polyethylene terephthalate, polyethylene naphthalate, polyethersulfone, polyamide, polyimide, polycarbonate, cellulose triacetate or polyether imide. When a resin film or paper is applied, a device can have flexibility. The device becomes flexible and light, and the practical performance thereof can be improved. The thickness of a substrate is usually 1 μm to 10 mm and preferably 5 μm to 5 mm.

A source electrode 1, drain electrode 3 and gate electrode 5 may be from a conductive material. Examples of the material include a metal such as platinum, gold, silver, aluminium, chromium, tungsten, tantalum, nickel, cobalt, copper, iron, lead, tin, titanium, indium, palladium, molybdenum, magnesium, calcium, barium, lithium, potassium and sodium and an alloy containing two or more of them; a conductive oxide such as $InO_2$, $ZnO_2$, $SnO_2$ and ITO; a conductive polymer compound such as polyaniline, polypyrrole, polythiophene, polyacetylene, polyparaphenylene, vinylene and polydiacetylene; semiconductors such as silicon, germanium and gallium arsenide; and a carbon material such as carbon black, fullerene, carbon nanotube, graphite and graphene. A conductive polymer compound and semiconductor may be doped. Examples of the dopant include an inorganic acid such as hydrochloric acid and sulfuric acid; an organic acid having an acidic functional group such as sulfonic acid; a lewis acid such as $PF_5$, $AsF_5$ and $FeCl_3$; a halogen atom such as iodine; and a metal atom such as lithium, sodium and potassium. Boron, phosphorus and arsenic are frequently used as a dopant for an inorganic semiconductor such as silicon.

Furthermore, a composite material containing carbon black or metal particles dispersed into the dopant may be used as a conductive material. To reduce contact resistance of a source electrode 1 and a drain electrode 3, which are in direct contact with a semiconductor, it is important to selecte appropriate work functions or to apply a surface treatment to the electrodes.

In addition, structures such as the distance (channel length) between the source electrode and the drain electrode and the width thereof (channel width) are important factors for determining the characteristics of a device. The channel length is usually 0.01 to 300 μm and preferably 0.1 to 100 μm. As the channel length is short, the amount of outputted current increases, but it conversely causes a short channel effect such as an effect on contact resistance and makes it difficult to control, a proper channel length is required. The width (channel width) between the source and drain electrode is usually 10 to 10000 μm and preferably 100 to 5000 μm. If an electrode has a comb structure or the like, the width of the channel can be increased. A channel can have an appropriate length in consideration of a requisite current amount and the structure of the element.

The structures (shapes) of a source electrode and a drain electrode each will be described. The structures of a source electrode and a drain electrode may be the same or different.

In the case of a bottom contact structure, individual electrodes can be generally formed by a lithographic method. Each electrode may be preferably formed into a rectangular parallelepiped shape. Recently various printing methods have been improved in terms of printing accuracy. Thus, an electrode has been able to be accurately formed by means of inkjet printing, gravure printing, screen printing or the like. In the case of a top contact structure where electrodes are formed on a semiconductor, vapor deposition can be performed using a shadow mask or the like. An electrode pattern can be directly printed and formed by means of inkjet printing or the like. The length of an electrode may be the same as the channel width mentioned above. The width of an electrode is not particularly defined, but the shorter the width, the more preferable in order to reduce the area of an element as long as electric characteristics can be stabilized. The width of an electrode is usually 0.1 to 1000 μm and preferably 0.5 to 100 μm. The thickness of an electrode is usually 0.1 to 1000 nm, preferably 1 to 500 nm and more preferably 5 to 200 nm. To electrodes 1, 3, 5, wirings are connected. The wirings may be formed from substantially the same materials as those for the electrodes.

An insulating layer 4 can be from a material having an insulating property. Examples of the material include polymers such as polyparaxylylene, polyacrylate, polymethyl methacrylate, polyolefines, polystyrene, polyvinyl phenol, polyamide, polyimide, polycarbonate, polyester, polyvinyl alcohol, polyvinyl acetate, polyurethane, polysulfone, fluoro resin, epoxy resin and phenolic resin and copolymers thereof in combination; metal oxides such as silicon dioxide, aluminum oxide, titanium oxide and tantalum oxide; ferroelectric metal oxides such as $SrTiO_3$ and $BaTiO_3$; dielectric substances such as nitrides, e.g., silicon nitride and aluminum nitride, sulfides, and a fluoride; or a polymer in which particles of these dielectric substances are dispersed. To reduce leak current, an insulating layer may preferably have high electrical insulation characteristics. As a result, a film thickness can be reduced, and capacitance can be increased, with the result that the amount of outputted current increases. To improve the mobility of a semiconductor, an insulating layer may preferably have a decreased surface energy; in other words, the insulating layer may be preferably a film having a smooth surface with less roughness. To attain this, a self-organized single molecular film and two insulating layers may be formed. The film thickness of an insulating layer 4 varies depending upon the material, but it is usually 0.1 nm to 100 μm, preferably 0.5 nm to 50 μm and more preferably 1 nm to 10 μm.

A material for a semiconductor layer 2 can be a heterocyclic compound represented by the general formula (1) of the present invention. The semiconductor layer 2 is made of the heterocyclic compound to form a thin film by means of the aforementioned method. For the purpose of e.g., improving characteristics of a thin-film transistor and adding other characteristics, other organic semiconductor materials and various types of additives may be, as necessary, added.

A thin-film transistor can comprise at least one heterocyclic compound represented by the general formula (1) as an organic semiconductor material. When a thin film is formed from a compound represented by the general formula (1) by a wet process, in other words, by use of a solvent, it is preferable that the film is used after a solvent is substantially evaporated from the film. A thin film can be also formed from the organic semiconductor material by a dry process, i.e., a vapor deposition method. For the purpose of improving characteristics of a transistor or the like, an additive such as a dopant can be also added.

The additives mentioned above may be added within the range of usually 0.01 to 10 wt %, preferably 0.05 to 5 wt % and more preferably 0.1 to 3 wt % relative to the total amount of organic semiconductor material as 1.

Furthermore, the semiconductor layer may consist of a plurality of layers. The thinner the film thickness of a semiconductor layer 2, the more preferable, as long as a requisite function is maintained. This is because, in horizontal thin-film transistors as shown in A, B and D, the characteristics of the elements do not depend upon the film thickness as long as the film has a predetermined thickness or more; on the other hand, as the film thickness increases, leakage current may increase. To exert a requisite function, the film thickness of a semiconductor layer is usually 1 nm to 1 μm, preferably 5 nm to 500 nm, and more preferably 10 nm to 300 nm.

For a thin-film transistor, if necessary, an additional layer may be provided, for example, between a substrate layer and an insulating film layer, between an insulating film layer and a semiconductor layer, or on the outer surface of the element,. For example, a protective layer may be formed on an organic semiconductor layer directly or via another layer, and it can reduce the effect of the ambient air such as humidity. Such an additional layer can also increase the ON/OFF ratio of a thin-film transistor element. Likewise, electric characteristics can be advantageously stabilized.

Examples of the material for the protective layer preferably include, but are not particularly limited to, various types of resins such as an epoxy resin, an acrylic resin, e.g., polymethyl methacrylate, polyurethane, polyimide, polyvinyl alcohol, fluorine resin and polyolefin; and dielectric substance such as inorganic oxide and a a nitride, e.g., silicon oxide, aluminum oxide and silicon nitride. Particularly, a resin (polymer) having less oxygen and water permeability and less water absorption ability is preferable. A gas barrier protective material developed for an organic EL display can be used. The film thickness of a protective layer can be optionally selected depending upon the purpose thereof, but it is usually 100 nm to 1 mm.

Thin-film transistor properties can be also improved by previously applying a surface modification or a surface treatment to a substrate or an insulating layer on which an organic semiconductor layer is laminated. For example, controlling the hydrophilic/hydrophobic rate of a substrate surface can allow the film formed on the substrate to be improved in film properties and film formation. Particularly, the organic semiconductor material may sometimes change in characteristics depending upon the condition of the film such as molecular orientation. For instance, when a surface treatment is applied to a substrate and an insulating layer, the molecular orientation of an interface portion between, for example, the substrate and an organic semiconductor layer to be formed thereon is controlled, and the number of trap sites on the substrate or the insulating layer is reduced. As a result, characteristics such as carrier mobility would be improved.

The trap site refers to a functional group such as a hydroxy group on an untreated substrate. If such a functional group is present, electrons are attracted to the functional group, with the result that carrier mobility is reduced. Therefore, it is often effective to reduce the number of trap sites for improving characteristics such as carrier mobility.

Examples of the surface treatment for improving characteristics as mentioned above include: self-organized single molecular film treatment with hexamethyldisilazane, octyltrichlorosilane, octadecyltrichlorosilane, octylphosphonic acid, octadecylphosphonic acid, decyl thiol or the like; a surface treatment with a polymer or the like, an acid treatment with hydrochloric acid, sulfuric acid, acetic acid or the like; an alkali treatment with sodium hydroxide, potassium hydroxide, calcium hydroxide, ammonia or the like; an ozone treatment; a fluorination treatment; a plasma treatment with oxygen plasma, argon plasma or the like; a treatment by forming a Langmuir-Blodgett film; a treatment by forming a thin film of another insulating material or a semiconductor; a mechanical treatment, an electric treatment with corona discharge or the like; a rubbing treatment with fiber or the like; and a combination thereof.

In these embodiments, for example, a method of forming a substrate layer and an insulating film layer, or an insulating film layer and an organic semiconductor layer may be appropriately selected from a vacuum vaporization method, a sputter method, a coating method, a printing method and a sol-gel method.

Next, a method for manufacturing the thin-film transistor device according to the present invention will be described. Herein, as an example, a method for manufacturing a top contact bottom gate type thin-film transistor shown in FIG. 1, embodiment example B will be described referring to FIG. 2. It is to be noted that the manufacturing method can be also applied to the thin-film transistors of other embodiments as mentioned above or the like.

Re: Substrate of Thin-Film Transistor and Substrate Treatment

Figure 2:
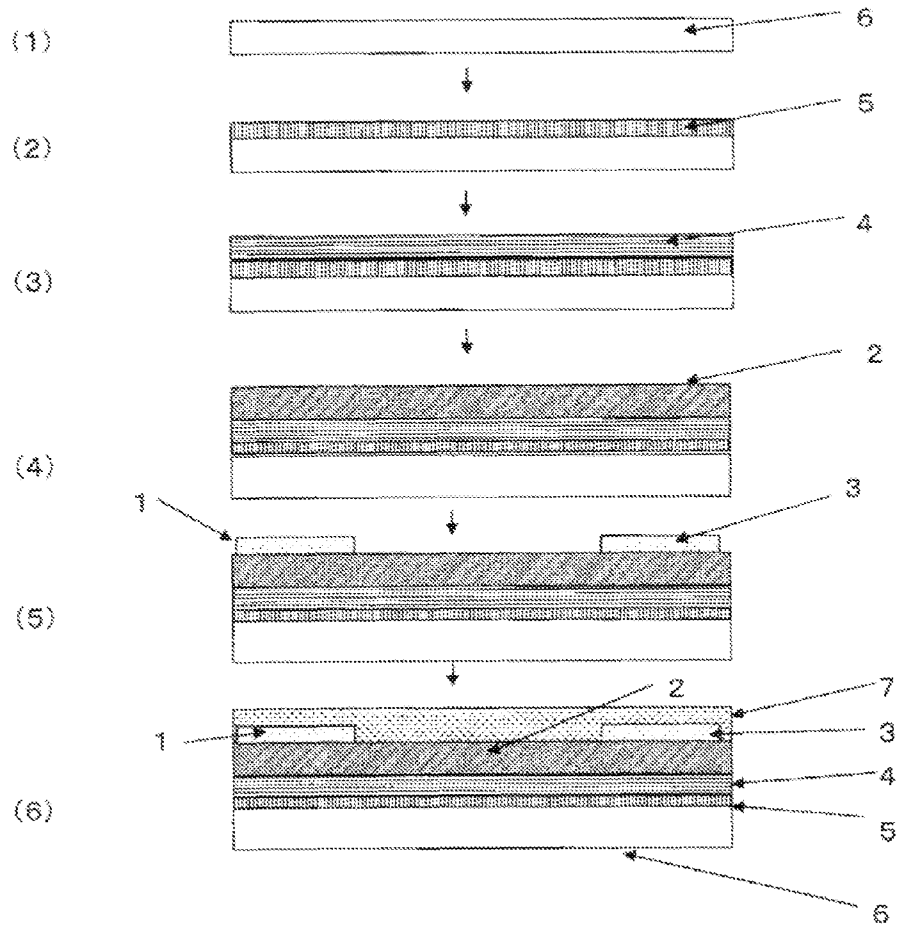
FIG. 2 a schematic view showing the process of manufacturing a thin-film transistor accorong to an embodiment of the present invention.

A thin-film transistor of the present invention is manufactured by forming various requisite layers and electrodes on a substrate 6 (see FIG. 2 (1)). A substrate can contain the aforementioned materials. Onto a substrate, e.g., the aforementioned surface treatments can be applied. The thinner the thickness of a substrate 6, the more preferable, as long as a requisite function is maintained. Although the thickness varies depending upon the material, it is usually 1 μm to 10 mm and preferably 5 μm to 5 mm. A substrate may further have a function of an electrode.

Re: Formation of Gate Electrode

A gate electrode 5 may be formed on a substrate 6 (see FIG. 2 (2)). The aforementioned materials can be used as an electrode material. An electrode film can be formed by various methods. Examples thereof include a vacuum vaporization method, a sputter method, a coating method, a hot printing method, a printing method and a sol-gel method. During or after film formation, if necessary, patterning may be performed so as to form a desired shape. Patterning can be performed by various methods, including a photolithographic method in which patterning and etching of a photoresist are combined. Also, patterning can be performed by a vapor deposition method using a shadow mask, a sputtering method, a printing method such as an inkjet printing, a screen printing, an offset printing and a relief printing, a soft lithographic method such as a micro contact printing method, or a combination thereof. The film thickness of a gate electrode 5 varies depending upon the material, but it is usually 0.1 nm to 10 μm, preferably 0.5 nm to 5 μm and more preferably 1 nm to 3 μm. In the case that a gate electrode also acts as a substrate, the film thickness may be larger than the aforementioned one.

Re: Formation of Insulating Layer

An insulating layer 4 may be formed on a gate electrode 5 (see FIG. 2 (3)). An insulating material can be as described above. An insulating layer 4 can be formed by various methods. Examples thereof include a coating method such as spin coating, spray coating, dip coating, cast, bar coating and blade coating; a printing method such as a screen printing, an offset printing and an inkjet printing; and a dry process such as a vacuum vaporization method, a molecular beam epitaxial growth method, an ion cluster beam method, an ion plating method, a sputtering method, an atmospheric pressure plasma method and a CVD method. In addition, included are a sol-gel method, and a method for forming an oxide film on a metal such as an alumite film on aluminum and a dioxide silicon film on silicon, for instance, by a thermal oxidation methodology. Note that, in the area where an insulating layer and a semiconductor layer come into contact with each other, a predetermined surface treatment may be applied to the insulating layer to satisfactorily orient molecules constituting a semiconductor, e.g., molecules of a compound represented by the formula (1), at the interface between both layers. The surface treatment method may be the same as those applied to a substrate. The quantity of outputted electricity can be increased by increasing the electrical capacitance of an insulating layer 4. Thus, the film thickness of an insulating layer 4 may be preferably reduced as much as possible. In this case, as the thickness of a film is reduced, the amount of leak current increases. Thus, the thickness of a film may be preferably reduced as long as the function of the film is maintained. The film thickness is usually 0.1 nm to 100 μm, preferably 0.5 nm to 50 μm and more preferably 5 nm to 10 μm.

Re.Formation of Organic Semiconductor Layer

An organic semiconductor material containing a heterocyclic compound represented by the general formula (1) of the present invention is used for forming an organic semiconductor layer (see FIG. 2 (4)). A film of an organic semiconductor layer can be formed by various methods. Specifically, examples of the method include a vacuum-process such as a sputtering method, a CVD method, a molecular beam epitaxial growth method and a vacuum vaporization method; and a coating method such as a dip coating method, a die coating method, a roll coating method, a bar coating method and a spin coating method; and a solution-process such as an inkjet method, a screen printing method, an offset printing method and a micro contact printing method.

First, a method for obtaining an organic semiconductor layer comprising forming a film of an organic semiconductor material by a vacuum process will be described. The method of forming the layer by a vacuum process may be preferably a vacuum vaporization method, and specifically a process comprising heating and vaporizing an organic semiconductor material as mentioned above in a crucible or a metal boat under vacuum, and allowing the vaporized organic semiconductor material to attach (deposit) onto a base (e.g., substrate, an insulating layer, a source electrode and a drain electrode). In the process, a vacuum degree is usually $1.0\times10^{-1}$ Pa or less and preferably $1.0\times10^{-3}$ Pa or less. Furthermore, it is preferable to carefully select substrate temperature because characteristics of the organic semiconductor film, or those of a thin-film transistor, may change depending upon the temperature of a substrate during vapor deposition. The substrate temperature during vapor deposition is usually 0 to 250° C., preferably 5 to 200° C., more preferably 10 to 180° C., further preferably 15 to 150° C. and particularly preferably 20 to 130° C.

Furthermore, the vapor deposition rate is usually 0.001 nm/second to 10 nm/second and preferably 0.01 nm/second to 1 nm/second. The film thickness of an organic semiconductor layer is usually 1 nm to 1 μm, preferably 5 nm to 500 nm and more preferably 10 nm to 300 nm.

In place of the vapor deposition method, in which an organic semiconductor material is heated and vaporized to be deposited on a substrate, other methods can be used to form an organic semiconductor layer.

Next, a method for obtaining an organic semiconductor layer by a solution process will be described. A heterocyclic compound represented by the general formula (1) of the present invention can be dissolved in a solvent or the like, and, if necessary, an additive can be added to the solution. The obtained composition can be applied to a substrate (insulating layer, exposed portions of a source electrode and a drain electrode). Examples of a coating method include a coating method such as casting, spin coating, dip coating, blade coating, wire-bar coating and spray coating; a printing method such as inkjet printing, screen printing, offset printing, flexo printing and relief printing; and a soft lithographic method such as micro contact printing, and a combination method thereof.

In addition, an analogous method to these coating methods can be also used, including a Langmuir-Blodgett method, in which ink as mentioned above is dropped on a water surface to form a single molecular film of an organic semiconductor layer, which is transferred and laminated onto a substrate; and a method of introducing a liquid crystal material or a molten material between two substrates with the help of a capillary action.

An environment such as the temperatures of a substrate and a composition during film formation time is important. Transistor characteristics may be changed due to the temperatures of a substrate and a composition. Thus, it is preferable that the temperatures of a substrate and a composition are carefully selected. The substrate temperature is usually 0 to 200° C., preferably 10 to 120° C. and more preferably 15 to 100° C. It is to be noted that the substrate temperature varies depending upon the solvent used in the composition.

The less the film thickness of the organic semiconductor layer formed by this method, the more preferable, as long as the function is maintained. As the film thickness increases, a risk of leakage current may increase. The film thickness of an organic semiconductor layer is usually 1 nm to 1 μm, preferably 5 nm to 500 nm and more preferably 10 nm to 300 nm.

The organic semiconductor layer thus formed (see FIG. 2 (4)) can be further improved in characteristics by a post treatment. For instance, a heat treatment allows an organic semiconductor property to be improved and stabilized because the treatment mitigats strain in a film arised during film formation, reduces the number of pin holes and allows alignment and orientation of a film to be controlled. Thus, it is effective to apply such a heat treatment in manufacturing a thin-film transistor of the present invention in order to improve its properties. The heat treatment is performed by heating a substrate after an organic semiconductor layer is formed. The temperature of a heat treatment is not particularly limited, but it is usually from room temperature to about 200° C., preferably from 40 to 150° C. and further preferably from 45 to 120° C. The time for a heat treatment is not particularly limited, but it is usually from 10 seconds to 24 hours and preferably about 30 seconds to 3 hours. The atmosphere for that may be air or an atmosphere of an inert gas such as nitrogen or argon. In addition, the shape of a film can be controlled by a solvent vapor.

Another post treatment method for an organic semiconductor layer may be applied, including a treatment with an oxidizing or reducing gas such as oxygen or hydrogen or an oxidizing or reducing liquid. The treatment allows change in characteristics to be induced to the layer through oxidation or reduction. For instance, the treatment can be applied to increase or reduce the density of a carrier in the film.

Furthermore, the properties of an organic semiconductor layer can be changed by a doping process, which comprises adding a small amount of element, atomic group, molecule or polymer to an organic semiconductor layer. For instance, the following can be doped: an acid such as oxygen, hydrogen, hydrochloric acid, sulfuric acid and sulfonic acid; a lewis acid such as $PF_5$, $AsF_5$ and $FeCl_3$; a halogen atom such as an iodine atom; a metal atom such as a sodium atom and a potassium atom; and an acceptor compound such as TCNQ and fullerene. The doping can be attained by bringing these gases into contact with an organic semiconductor layer, immersing an organic semiconductor layer in these solutions or applying an electrochemical doping treatment. These doping processes may not be performed after formation of an organic semiconductor layer. A dopant may be added during synthesis of an organic semiconductor compound. Alternatively, in a process where an organic semiconductor layer is formed from ink to manufacture an organic semiconductor element, a dopant can be added to the ink or in a step of forming a thin film. Furthermore, codeposition may be made by adding a material for use in doping to a material for forming an organic semiconductor layer by vapor deposition. Furthermore, a doping material may be mixed with an ambient atmosphere where an organic semiconductor layer is formed (whereby an organic semiconductor layer can be formed under an ambient atmosphere containing a doping material). Furthermore, ions accelerated in vacuum can be bombarded to a film, thereby doping them into a film.

Examples of the effect of these doping processes include a change in electric conductivity due to an increase or decrease of a carrier density, a change in polarity of carrier (p-type, n-type) and a change in the Fermi level.

Re. Formation of Source Electrode and Drain Electrode

A source electrode 1 and drain electrode 3 are formed, for instance, in accordance with a method for forming a gate electrode 5 (see FIG. 2 (5)). Various additives can be used to reduce contact resistance with an organic semiconductor layer.

Re. Protective layer

Formation of a protective layer 7 on an organic semiconductor layer is advantageous because the ambient atmospheric effect can be minimized and the electric characteristics of an organic thin-film transistor can be stabilized (see FIG. 2 (6)). A material for the protective layer is as mentioned above. The film thickness of a protective layer 7 may be selected depending upon the purpose, but it is usually 100 nm to 1 mm.

Various methods can be employed in forming a protective layer. In the case that a protective layer is formed from a resin, for instance, the following may be employed: a method of applying a resin solution and drying it to form a resin film; and a method of applying or depositing a resin monomer and then polymerizing it. After the film is formed, a crosslinking treatment may be applied. In the case that a protective layer is formed from an inorganic material, for instance, the following may be employed: a vacuum process such as a sputtering method and a vapor deposition method; and a solution process such as a sol-gel method.

In an thin-film transistor, a protective layer can be provided not only on an organic semiconductor layer but also between individual layers, if necessary. These layers may be helpful to stabilize electric characteristics of a thin-film transistor.

Since a heterocyclic compound represented by the above general formula (1) is used as an organic semiconductor material, a thin-film transistor can be manufactured by a relatively low temperature process. Therefore, a flexible material, such as a plastic plate and a plastic film, which has not been used under conditions exposed to high temperature, can be used as a substrate. As a result, an irrefrangible element with a light weight and an excellent flexibility can be manufactured and can be used as e.g., a switching device of an active matrix of a display.

The thin-film transistor can be used also as digital elements and analog elements such as a memory circuit element, a signal driver circuit element and a signal processing circuit element. Furthermore, they are used in combination to form a display, an IC card, an IC tag or the like. Furthermore, the thin-film transistor, since change in characteristics thereof can be caused by external stimulation such as a chemical substance, can be used an FET sensor.

Next, organic EL device will be described.

An organic EL element has attracted attention by the characteristics that it is can be applied in a solid form to a self-luminous large-area color display, lighting and the like, and lots of elements have beed developed. The structure of an organic EL element may be a structure comprising two layers of a light emitting layer and a charge transport layer between opposed electrodes consisting of cathode and an anode; a structure comprising three layers of an electron transport layer, a light emitting layer and a hole transport layer laminated between the opposed electrodes; or a structure comprising three layers or more between the opposed electrodes. It may be also a structure comprising a light emitting layer as a single layer.

The hole transport layer is a layer for allowing holes to be injected from an anode, and transporting the holes to a light emitting layer, and has a function of facilitating injection of holes to a light emitting layer and a function of blocking electrons. Furthermore, the electron transport layer is a layer for allowing electrons to be injected from a cathode, and transporting the electrons to a light emitting layer, and has a function of facilitating injection of electrons to a light emitting layer and a function of blocking holes.

In the light emitting layer, the electrons and holes separately injected are reunited to generate excitons. Energy is emitted in the process where the excitons radiate and lose activity. This energy is detected as emission of light. Now, preferable embodiments of the organic EL element will be described below.

An organic EL element is an element having a single or a plurality of organic thin films between anode and cathode electrodes, and emitting light by electric energy.

An anode that can be used in the organic EL element is an electrode having a function of injecting holes into a hole injection layer, a hole transport layer and a light emitting layer. Generally, a metal oxide, a metal, an alloy and a conductive material having a work function of 4.5 eV or more are suitable for the anode. Examples thereof include, but are not particularly limited to, a conductive metal oxide such as tin oxide (NESA), indium oxide, indium tin oxide (ITO) and indium zinc oxide (IZO), a metal such as gold, silver, platinum, chromium, aluminium, iron, cobalt, nickel and tungsten, an inorganic conductive substance such as copper iodide and copper sulfide, a conductive polymer such as polythiophene, polypyrrole and polyaniline and carbon. Among them, ITO and NESA are preferable.

An anode may be formed from, if necessary, a plurality of materials and constituted of two layers or more. The resistance of an anode is not limited as long as sufficient current for light emission of an element can be supplied, but it is preferably lower in view of power consumption of the device. For example, an ITO substrate having a sheet resistance value of 300 Ω/□ or less would function as an electrode. However, a substrate having a sheet resistance value of several Ω/□ has been available, and it is thus desirable to select a substrate having low resistance and high transmissivity. The thickness of an ITO substrate can be optionally selected depending on a resistance value, but it may be usually in the range of between 5 and 1000 nm and preferably between 10 and 500 nm. Examples of a method for forming a film such as ITO include a vapor deposition method, an electron beam method, a sputtering method, a chemical reaction method and a coating method.

A cathode that can be used in the organic EL device is an electrode having a function of injecting electrons into an electron injection layer, an electron transport layer and a light emitting layer. Generally, a metal and an alloy having a small work function (about 4 eV or less) are suitable for that cathode. Examples thereof include, but are not particularly limited to, platinum, gold, silver, copper, iron, tin, zinc, aluminium, indium, chromium, lithium, sodium, potassium, calcium and magnesium. To improve element characteristics by increasing an electron injection efficiency, lithium, sodium, potassium, calcium and magnesium are preferable. An alloy include an alloy with a metal having a low work function including aluminium or silver. Alternatively, these may be laminated to form the electrode structure. An electrode of a layered-structure may be composed of an inorganic salt such as lithium fluoride. If emission light is taken out not from the anode side but from the cathode side, a transparent electrode, which can be formed from e.g., ITO at a temperature as low as possible, can be employed. Examples of a film-formation method include, but are not particularly limited to, a vapor deposition method, an electron beam method, a sputtering method, a chemical reaction method and a coating method. The resistance of a cathode is not limited as long as sufficient current for light emission of an element can be supplied, but it is preferably lower in view of power consumption of the element. Specifically, several hundreds to several Ω/□ is preferable. The film thickness usually falls within the range of 5 to 1,000 nm and preferably 10 to 500 nm.

For the purpose of sealing and protection, a cathode may be protected by an oxide or a nitride such as titanium oxide, silicon nitride, silicon oxide, silicon oxynitride and germanium oxide or a mixture thereof, polyvinyl alcohol, vinyl chloride, a hydrocarbon polymer or a fluorine polymer, and sealed together with a dehydrating agent such as barium oxide, phosphorus pentoxide and calcium oxide.

To take out light emission, it is preferable to form an electrode on a substrate having transparency generally within a light emission wavelength range of an element. Examples of a transparent substrate include a glass substrate and a polymer substrate. A glass substrate may be from soda lime glass, non-alkali glass or quartz. A glass substrate may have a thickness sufficient to keep mechanical/thermal strength, preferably a thickness of 0.5 mm or more. A glass material may be preferably a material having less ion elution. Non-alkali glass is more preferable. As a glass material having such a property, soda lime glass having a barrier coating of e.g., $SiO_2$ is commercially available. Examples of a polymer substrate include polycarbonate, polypropylene, polyethersulfone, polyether imide, polyethylene terephthalate, polyethylene naphthalate, polyimide, polyamide, and acryl substrate.

An organic thin film of an organic EL element is composed of a single layer or a plurality of layers between anode and cathode electrodes. A heterocyclic compound represented by the general formula (1) is added to the organic thin film, which allows an obtained element to emit light by electric energy.

The "layer" of a single layer or a plurality of layers constituting an organic thin film refers to a hole transport layer, an electron transport layer, a hole transport light emitting layer, an electron transport light emitting layer, a hole block layer, an electron block layer, a hole injection layer, an electron injection layer, a light emitting layer or a single layer having the functions possessed by these layers, as shown in the following structural example 9). In the present invention, examples of the structure of a layer constituting an organic thin film include the following structural examples 1) to 9). Any of the structures may be employed.

Structural Examples

1) Hole transport layer/electron transport light emitting layer.

2) Hole transport layer/light emitting layer/electron transport layer.

3) Hole transport light emitting layer/electron transport layer.

4) Hole transport layer/light emitting layer/hole block layer.

5) Hole transport layer/light emitting layer/hole block layer/electron transport layer.

6) Hole transport light emitting layer/hole block layer/electron transport layer.

7) Structure formed by adding a single hole injection layer to each of the structures 1) to 6) before the formation of the hole transport layer or the hole transport light emitting layer.

8) Structure formed by adding a single electron injection layer to each of the structures 1) to 7) before the formation of the electron transport layer or the electron transport light emitting layer.

9) Structure consisting of a single layer containing the mixture of the materials constituting the layers of each of the structures 1) to 8).

The structure 9) may consist of a single layer made of a material generally called a bipolar light emitting material; or a single layer containing a light-emitting material, and a hole transport material or an electron transport material. Generally, a multi-layer structure allows charges, i.e., holes and/or electrons, to be efficiently transported and reunited. Furthermore, quenching of charges can be suppressed, thereby preventing stability of an element from decreasing and improving efficiency of light emission.

A hole injection layer and transport layer are formed by laminaing a hole transport material alone or a mixture of two or more hole transport materials. Examples of a hole transport material preferably include a triphenyl amine such as N,N'-diphenyl-N,N'-di(3-methylphenyl)-4,4'-diphenyl-1,1'-diamine and N,N'-dinaphthyl-N,N'-diphenyl-4,4'-diphenyl-1,1'-diamine; a heterocyclic compound such as a bis(N-allylcarbazole), a bis(N-alkylcarbazole), a pyrazoline derivative, a stilbene compound, a hydrazone compound, a triazole derivative, an oxadiazole derivative and a porphyrin derivative; and a polymer such as a polycarbonate and a styrene derivative having a monomer as mentioned above as a side chain, polyvinylcarbazole and polysilane. A hole transport material is not particularly limited as long as it can form a thin film required for the element and is capable of injecting holes from an electrode and transporting holes. A hole injection layer, which is provided between a hole transport layer and an anode to improve a hole injection property, may be formed from a phthalocyanine derivative, a star burst amine such as m-MTDATA, and a polymer such as a polythiophene (e.g., PEDOT) and a polyvinylcarbazole derivative.

An electron transport material is required to efficiently transport electrons between the electrodes to which an electric field is applied and from the negative electrode. An electron transport material preferably has high electron injection efficiency and efficiently transports electrons injected. Accordingly, an electron transport material is required to have high electron affinity, large electron mobility and excellent stability, and to generate few impurities acting as a trap during manufacturing and use. Examples of such a substance satisfying these conditions include, but are not particularly limited to, a quinolinol derivative/metal complex represented by tris(8-quinolinolato)aluminium complex, a tropolone/metal complex, a perylene derivative, a perinone derivative, a naphthalimide derivative, a naphthalic acid derivative, an oxazole derivative, an oxadiazole derivative, a thiazole derivative, a thiadiazole derivative, a triazole derivative, a bisstyryl derivative, a pyrazine derivative, a phenanthroline derivative, a benzoxazole derivative and a quinoxaline derivative. These electron transport materials can be used alone or in combination with another electron transport material in the form of a laminate or as a mixture. Examples of an electron injection layer, which is provided between an electron transport layer and a cathode to improve electron injection property, include a metal such as cesium, lithium and strontium, and lithium fluoride.

An hole block layer is formed from a hole block substance alone or two types or more hole block substances in the form of a laminate or as a mixture. Examples of a hole block substance preferably include a phenanthroline derivative such as bathophenanthroline and bathocuproine, a silole derivative, a quinolinol derivative/metal complex, an oxadiazole derivative and an oxazole derivative. A hole block substance is not particularly limited as long as it is capable of blocking holes from discharging out of an element from the cathode side, thereby preventing luminous efficiency from decreasing.

A light emitting layer refers to an organic thin film which emits light and includes a hole transport layer, an electron transport layer or a bipolar transport layer which is capable of emitting intensive light. A light emitting layer may be only formed from a light-emitting material (e.g., host material, dopant material). This may be either a mixture of a host material and a dopant material or a host material alone. Each of a host material and a dopant material may be a single material or a mixture of plurality of materials.

A dopant material may be contained either wholly or partly in the host material. A dopant material may be either laminated or dispersed. Examples of a light emitting layer include a hole transport layer and an electron transport layer as mentioned above. Examples of the materials for a light emitting layer include a carbazole derivative, an anthracene derivative, a naphthalene derivative, a phenanthrene derivative, a phenylbutadiene derivative, a styryl derivative, a pyrene derivative, a perylene derivative, a quinoline derivative, a tetracene derivative, a perylene derivative, a quinacridone derivative, a coumarin derivative, a porphyrin derivative, and a phosphorescence metal complex (e.g., Ir complex, Pt complex, Eu complex).

Examples of a method for forming an organic thin film of an organic EL element generally include a vacuum process such as resistance heating vapor deposition, electron beam vapor deposition, sputtering and a molecular stacking method; a solution process such as a coating method including casting, spin coating, dip coating, blade coating, wire-bar coating and spray coating; a printing method including inkjet printing, screen printing, offset printing and relief printing; a soft lithographic method including a micro contact printing method; and a combination of these methods. The thickness of each layer varies depending upon the resistance values/charge mobility of individual substances. Thus, it is not particularly limited but selected from the range between 0.1 and 500 nm, preferably between 0.5 and 300 nm and more preferably between 1 and 100 nm.

Of the organic thin films constituting an organic EL element according to the present invention, a single or a plurality of thin films including a light emitting layer, a hole transport layer or an electron transport layer present between an anode electrode and an cathode electrode can contain a heterocyclic compound represented by the general formula (1), thereby obtaining a element efficiently emitting light even at low electric energy.

The element can be thus obtained by forming a single or a plurality of layers containing a heterocyclic compound represented by the general formula (1) between an anode and a cathode. It is not particularly limited what parts a compound represented by the general formula (1) is provided for, but the heterocyclic compound can be preferably provide for a hole transport layer or a light emitting layer or used as a host material in combination with a dopant material.

A heterocyclic compound represented by the above general formula (1) can preferably constitute a hole transport layer or a light emitting layer. The heterocyclic compound can be also combined or mixed with an electron transport material or a hole transport material and a light-emitting material or as a mixture.

When a heterocyclic compound represented by the above formula (1) is used as a host material in combination with a dopant material, examples of the dopant material specifically include, but are not limited to, a perylene derivative such as bis(diisopropyl phenyl)perylenetetracarboxylic imide, a perinone derivative, 4-(dicyanomethylene)-2-methyl-6-(p-dimethylaminostyryl)-4H-pyran (DCM) and its analogue, a metal phthalocyanine derivative such as magnesium phthalocyanine and aluminium chlorophthalocyanine, a rhodamine compound, a deazaflavin derivative, a coumarin derivative, an oxazine compound, a squarylium compound, a violanthrone compound, Nile red and a pyrromethene derivative such as 5-cyanopyrromethene-BF4 complex. Furthermore, included are a phosphorescence material such as an Eu complex containing acetyl acetone or benzoyl acetone and phenanthroline as a ligand, and a porphyrin or ortho metal complex such as an Ir complex, an Ru complex, a Pt complex and an Os complex. When two types of dopant materials are mixed, an assist dopant such as rubrene can be contained to efficiently transfer energy from a host dye, thereby obtaining light emission with improved color purity. In either case, a dopant having a high fluorescence quantum yield can be preferably contained to obtain high brightness property.

If a dopant material is contained too much, a concentration quenching phenomenon occurs. Thus, a dopant material may be contained usually in an amount of 30 mass % or less relative to a host material, preferably 20 mass % or less, further preferably 10 mass % or less. A method of doping a dopant material to a host material in a light emitting layer may be performed by co-depositing the dopant with the host material. A dopant material may be also previously mixed with a host material, and the mixture may be subjected to co-vapor deposition. The doping can be also performed by sandwiching a host material between dopant materials. In this case, a single or two or more dopant layers may be laminated with a host material layer.

These dopant layers may each form a layer alone, or the dopante material may be mixed. Furthermore, a dopant material can be dissolved or dispersed in a polymer binder such as a solvent-soluble resin including polyvinyl chloride, polycarbonate, polystyrene, polystyrene sulfonic acid, poly(N-vinylcarbazole), poly(methyl)(metha)acrylate, polybutyl methacrylate, polyester, polysulfone, polyphenylene oxide, polybutadiene, a hydrocarbon resin, a ketone resin, a phenoxy resin, polysulfone, polyamide, ethylcellulose, vinyl acetate, an ABS resin and a polyurethane resin; or a hardening resin including a phenolic resin, a xylene resin, a petroleum resin, a urea resin, a melamine resin, an unsaturated polyester resin, an alkyd resin, an epoxy resin and a silicone resin.

The organic EL element can be suitably applied to a flat panel display. It can be further applied to a flat a backlight. In this case, the element can be applied to not only a backlight emitting color light but also a backlight emitting white light. A backlight is principally used for the purpose of improving visibility of a display apparatus not emitting light by itself, and applied to e.g., a liquid crystal display apparatus, a clock, an audio instrument, an automobile panel, a display board and an indicator. Particularly, a conventional backlight for use in a liquid crystal display apparatus, in particular, for a personal computer (reducing thickness remains a problem) has been composed of a fluorescent light or a light guide plate, which makes it difficult to reduce the thickness. However, a backlight composed of a light-emitting element of the present invention is characterized by being thin and light and can thus overcome the problem. Similarly, an organic EL device of the present invention can be advantageously applied to a lighting device.

A heterocyclic compound represented by the general formula (1) of the present invention can provide an organic EL display apparatus having a high luminous efficiency and a long life. Furthermore, thin-film transistor elements of the present invention can be combined to provide an organic EL display apparatus capable of electrically controlling an ON/OFF phenomenon of applied voltage with high accuracy at low cost.

Re: Organic Light Emitting Transistor

Now, an organic light emitting transistor will be described. A heterocyclic compound represented by the general formula (1) can be also applied to an organic light emitting transistor. A light emitting transistor in which an organic transistor and an organic electroluminescence element are combined, is constructed by integrating a driving circuit and a light emitting portion of a display, and the area occupied by the driving transistor circuit can be reduced, thereby increasing an aperture ratio of the display. More specifically, the number of parts can be reduced and a manufacturing process is simplified. Thus, a more inexpensive display can be provided. Light is emitted basically by simultaneously injecting electrons and holes from a source electrode and a drain electrode of an organic transistor, respectively, into an organic light emitting material and recoupling them. The amount of luminescence is controlled by the electric field from a gate electrode.

The structure thereof may be the same as described in the section of an organic transistor. In the structure a light emitting transistor material can be used in place of the semiconductor materials for an organic transistor. The material and the process to be used can be appropriately selected depending on the characteristics of a semiconductor compound, but the transistor preferably has a structure for taking out light to the exterior. For an organic transistor, it is generally sufficient to inject either electrons or holes. On the other hand, in a light emitting transistor of the present invention, light is emitted by coupling electrons and holes in a semiconductor layer. A structure of facilitating effective injection of charge from electrodes, coupling them and light emission is preferable.

Re: Photoelectric Conversion Element

The semiconductor properties of a heterocyclic compound represented by the general formula (1) of the present invention can be employed for an organic photoelectric conversion element. Examples of the photoelectric conversion element include a solid-state imaging element such as a charge combining device (CCD), which has a function of converting a screen image signal of e.g., a motion picture or a stationary picture to a digital signal. An organic photoelectric conversion element is also expected to be more inexpensive, applicable to a large area process, and flexible, which is intrinsic to an organic substance.

Re: Organic Solar Cell Element

A heterocyclic compound represented by the general formula (1) of the present invention can be used to easily manufacture a flexible and inexpensive organic solar cell element. More specifically, the organic solar cell element is in a solid-state and characterized by flexibility and improved life. Conventionally, development of a solar cell containing an organic semiconductor thin film in combination with a conductive polymer or fullerene has been in a main stream, but the solar cell has a problem with a photoelectric conversion efficiency.

In general, an organic solar cell element is constructed in the same manner as in a silicon solar cell, i.e., by sandwiching a layer generating power (a power generating layer) between an anode and a cathode. The element functions as a solar cell by absorbing light to generate holes and electrons and receives the holes and electrons at each of the electrodes. The power generation layer thereof may be composed of a P-type donor material, an N-type acceptor material and other materials (e.g., buffer layer). If these materials are organic materials, the resultant solar cell is referred to as an organic solar cell.

Figure 3:
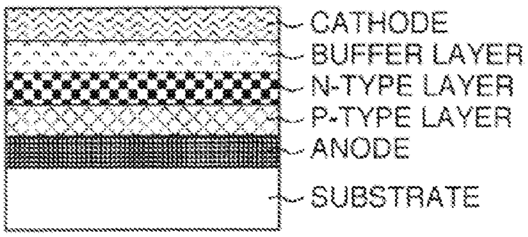
FIG. 3 is a schematic view of a structure to be applied to a photoelectric conversion element and a solar cell.
Figure 4:
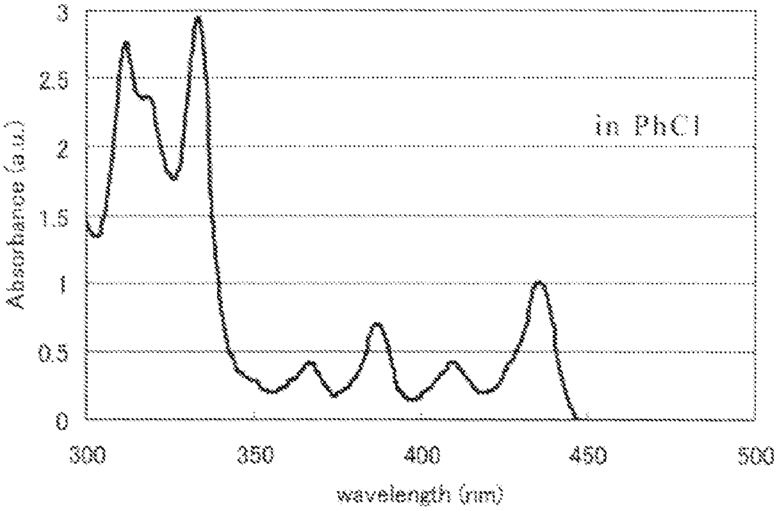
FIG. 4 shows an ultraviolet/visible light absorption spectrum of a compound of formula (10) in chlorobenzene.
Figure 5:
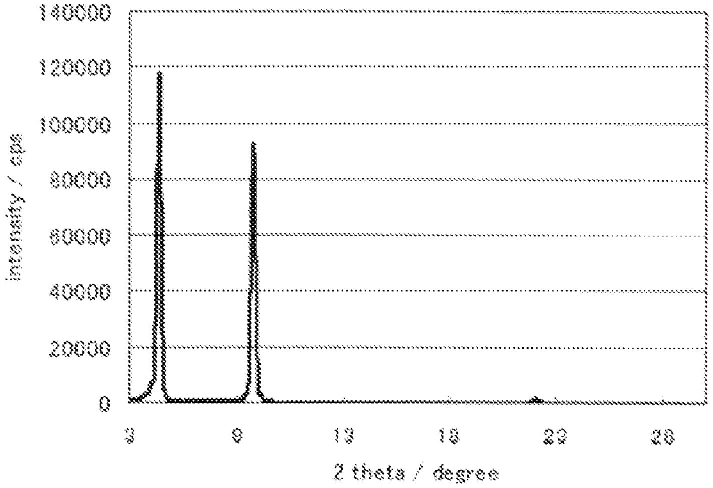
FIG. 5 shows an out-of-plane X-ray diffraction curve of a vapor deposition film of the compound (10) formed on $SiO_2$.
Figure 6A:
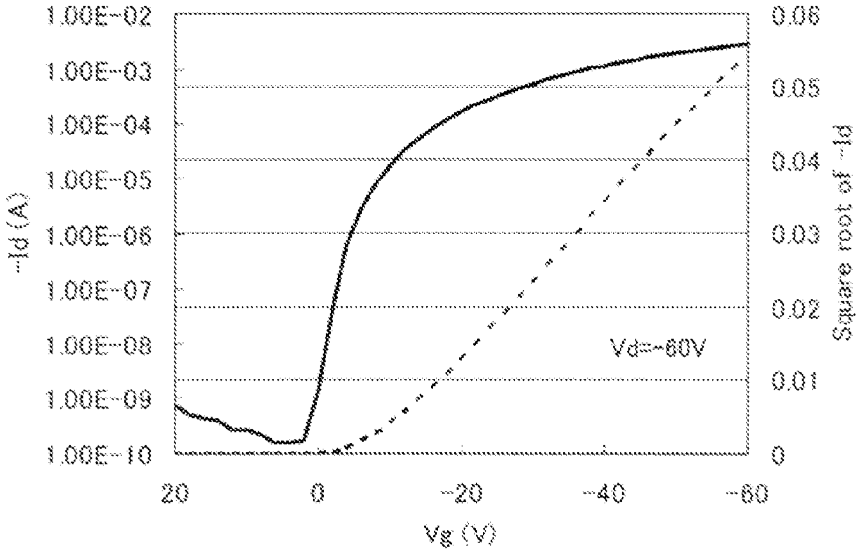
FIG. 6 shows transfer characteristic (A) and output characteristic (B) of a field effect transistor demonstrated in Example 1.
Figure 6B:
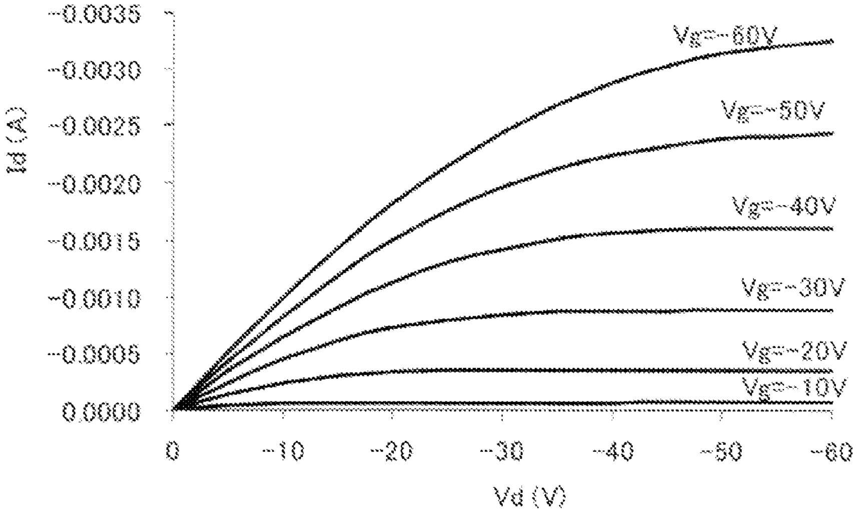

Examples of the structure thereof include Schottky junction, heterojunction, bulk heterojunction, nanostructure junction and hybrid. The element functions as a solar cell by efficiently absorbing incident light by the individual materials, generating charges, separating the charges into holes and electrons, transporting the holes and electrons and collecting them. As an example, the structure of a heterojunction element, which is a general solar cell, is shown in FIG. 3.

Now, components of an organic solar cell element will be described.

An anode and cathode of the organic solar cell element are the same as defined in an organic EL device as mentioned above. Since light has to be efficiently absorbed, an electrode is desirably transparent to light within a wavelength region absorbed by a power generation layer. In order to have satisfactory solar cell characteristics, it is preferable that the sheet resistance thereof is 20 Ω/□ or less, and the light transmissivity thereof is 85% or more.

The power generation layer is composed of a single or a plurality of organic thin films at least containing a compound represented by the general formula (1) of the present invention. An organic solar cell element may have the structure previously mentioned; however, it may be basically constructed of a P-type donor material, an N-type acceptor material and a buffer layer.

Examples of a P-type donor material include the same hole-transporting compounds as those for the hole injection layer and the hole transport layer as described in the section of an organic EL device, π conjugated polymers such as a polyparaphenylene vinylene derivative, a polythiophene derivative, a polyfluorene derivative and a polyaniline derivative; and polymers having a carbazole and other heterocyclic ring in a side chain. Examples of the P-type donor material further include low molecular weight compounds such as a pentacene derivative, a rubrene derivative, a porphyrin derivative, a phthalocyanine derivative, an indigo derivative, a quinacridon derivative, a merocyanine derivative, a cyanine derivative, a squarylium derivative and a benzoquinone derivative.

Examples of the N-type acceptor material include the same electron-transporting compounds as those for the electron transport layer as described in the section of an organic EL device; polymer materials such as an oligomer or polymer having pyridine or a derivative thereof as the skeleton, an oligomer or polymer having quinoline or a derivative thereof as the skeleton, a polymer having benzophenanthroline or a derivative thereof as the skeleton, and a cyanopolyphenylene vinylene derivative (e.g., CN-PPV); and low molecular weight materials such as a fluorinated phthalocyanine derivative, a perylene derivative, a naphthalene derivative, a bathocuproine derivative, and a fullerene derivative such as C60, C70 and PCBM.

Materials capable of efficiently absorbing light to generate charges are preferable, and materials having a high absorbance index are preferable.

A heterocyclic compound represented by the general formula (1) of the present invention can be preferably used particularly as a P-type donor material. A method for forming a thin film acting as a power generation layer of an organic solar cell is the same as previously described in the section of an organic EL device. The thickness of a thin film varies depending upon the structure of a solar cell. The thicker the film, the more preferable to sufficiently absorb light and prevent short circuit. On the other hand, the thinner the film, the more suitable to shorten the distance for transporting charges generated. In general, the thickness of a power generation layer is preferably about 10 to 500 nm.

Re: Organic Semiconductor Laser Element

A heterocyclic compound represented by the formula (1) of the present invention has an organic semiconductor property, and is expected to be applied to an organic semiconductor laser element.

More specifically, in an organic semiconductor device containing a compound represented by the general formula (1) of the present invention, a resonator structure is integrated and if a density in an excitation state can be sufficiently increased by efficiently injecting carriers, it is expected that light is amplified to emit laser. In the art, laser oscillation due to light excitation has been only observed. It is said that it is very difficult to produce a high-density excitation state by injecting highly dense carriers required for laser oscillation by electric excitation to an organic semiconductor element. However, it is expected that an organic semiconductor element containing a compound represented by the formula (1) of the present invention may generate highly efficient light emission (electroluminescence).

EXAMPLES

The present invention will be more specifically described referring to Examples, but the present invention is not limited to these Examples. In Examples, unless otherwise specified, "parts" represents parts by mass; % represents mass %; the numbers of formulas specifying compounds correspond to those specifically described in the above. Unless otherwise specified, the reaction temperatures indicate a temperature within a reaction system.

Compounds obtained in Synthesis Examples were, as necessary, subjected to measurements such as MS (mass analysis spectrum), NMR, elementary analysis, maximum absorption (λ max) and mp (melting point) to determine the structural formulas. Measurement instruments are as follows.

MS spectrum: ShimadzuQP-5050A

Absorption spectrum: ShimadzuUV-3150

$^1$H-NMRspectrum: JEOL Lambda 400 type

Synthesis Example 1

Synthesis of 2,7-bis(trimethylstannyl)naphtho[2,3-b:6,7-b']dithiophene (compound of formula (3))

Under a nitrogen atmosphere, n-BuLi (1.57N hexane solution, 5.7 ml, 8.9 mmol) was slowly added to an anhydrous THF (80 mL) solution of naphtho[2,3-b:6,7-b']dithiophene (a compound of formula (2)) (675 mg, 2.8 mmol) at −78° C. The reaction solution was heated and refluxed. After the reaction for 1.5 hours, the reaction solution was cooled to −78° C. To the reaction solution, trimethyltin chloride (2.24 g, 11.2 mmol) was added. After the mixture was stirred at room temperature for 11 hours, and water (100 mL) was added thereto. The resultant mixture was separated into phases. The water layer was extracted with methylene chloride (100 mL×3). The organic layer was dried over anhydrous magnesium sulfate ($MgSO_4$) and concentrated under reduced pressure. The resultant residue was recrystallized with acetone to obtain 2,7-bis(trimethylstannyl)naphtho[2,3-b:6,7-b'] dithiophene (861 mg, yield 54%) as a yellow solid substance.

$^1$H-NMR (400 MHz, $CDCl_3$) 0.48; (s, 18H), 7.49; (s, 2H), 8.35; (s, 2H), 8.48; (s, 2H); EIMS (70 eV) m/z=566 (M+)

Synthesis Example 2

Synthesis of 2,7-bis(2,2'-methylsulfinylbenzene)naphtho[2,3-b:6,7-b']dithiophene (compound of formula (5) where R is a hydrogen atom)

Under a nitrogen atmosphere, $Pd(PPh_3)_4$ (259 mg, 0.224 mmol) was added to a toluene (95 mL) solution of 2,7-bis(trimethylstannyl)naphtho[2,3-b:6,7-b']dithiophene (compound of formula (3)) (1.27 g, 2.24 mmol) and 2-bromomethylsulfinylbenzene (1.10 g, 5.00 mmol), which is a compound of formula (4) where R is a hydrogen atom. The reaction solution was heated to a reflux temperature and stirred for 62 hours. After completion of the reaction, the reaction solution was cooled to room temperature. The resultant solid matter was filtered and washed with water and ethanol to obtain 2,7-bis(2,2'-methylsulfinylbenzene)naphtho[2,3-b:6,7-b']dithiophene (5) (1.04 g, yield 90%) as a pale-green solid substance.

$^1$H-NMR (400 MHz, $CDCl_3$) 2.60; (s, 6H), 7.53; (s, 2H), 7.61-7.72; (m, 6H), 8.21; (brd, 2H), 8.43; (s, 2H), 8.50; (s, 2H); EIMS (70 eV) m/z=516 (M+)

Synthesis Example 3

Synthesis of bis[1]benzothieno[2,3-d:6,7-d']naphtho[2,3-b:6,7-b']dithiophene (compound of formula (10))

Under a nitrogen atmosphere, diphosphorus pentachloride (60 mg, 0.42 mmol) was added to trifluoromethanesulfonic acid (15 mL). The reaction solution was stirred for 20 minutes at room temperature. To this, 2,7-bis(2,2'-methylsulfinylbenzene)naphtho[2,3-b:6,7-b']dithiophene (compound of formula (5) where R is a hydrogen atom) (516 mg, 1.00 mmol) was added. The reaction solution was stirred at room temperature for 100 hours. After completion of the reaction, the reaction mixture was poured in ice water. The resultant precipitate was filtered off and washed with water to obtain a solid matter. The resultant solid matter was further subjected to a reflux in pyridine (30 mL) for 24 hours under a nitrogen atmosphere. To the reaction container, water was added. The resultant precipitate was filtered and washed with water, acetone and dichloromethane and thereafter placed in a Soxhlet extractor and washed with acetone and chloroform.

The solid substance was dried and purified by vacuum sublimation to obtain the compound of formula (10) (165 mg, yield 37%) as a yellow solid substance. EIMS (70 eV) m/z=452 (M+); Anal. Calcd for $C_{26}H_{12}S_4$: C, 68.99%; H, 2.67%. Found: C, 68.66%;H, 2.34%. λmax: 496 nm (thin film), 436 nm (Chlorobenzene)

Example 1

Formation of field effect transistor using a compound of formula (10)

An n-doped silicon wafer containing a $SiO_2$ thermal oxidation film with a thickness of 200 nm (surface resistance 0.02 Ω·cm or less) treated with octadecyltrichlorosilane was placed in a vacuum vapor deposition apparatus, which was evacuated until degree of vacuum in the apparatus reached $1.0\times10^{-3}$ Pa or less. In accordance with a resistance heating vapor deposition method, a compound of formula (10) was vapor-deposited onto the electrode to a thickness of 50 nm at a vapor deposition rate of 1 Å/sec at a substrate temperature of about 100° C. to form a semiconductor layer (2). Subsequently, to the substrate, a shadow mask for forming an electrode was attached. The resultant substrate was placed in a vacuum vapor deposition apparatus, which was evacuated until degree of vacuum in the apparatus reached $1.0\times10^{-4}$ Pa or less. By the resistance heating vapor deposition method, gold electrodes, which are a source electrode (1) and a drain electrode (3), were vapor-deposited to a thickness of 40 nm to obtain a TC (top contact) type field effect transistor (channel length 50 μm, channel width 1.5 mm) of the present invention.

In the field effect transistor of the Example, the thermal oxidation film of the n-doped silicon wafer has the function of an insulating layer (4) and the n-doped silicon wafer has the functions of a substrate (6) and a gate electrode (5) (see FIG. 1-B). The resultant field effect transistor was placed in a prober to measure a semiconductor property by a semiconductor parameter analyzer 4200SCS (manufactured by Keithley). To assess the semiconductor property, a drain current-gate voltage (transfer) characteristic was measured by scanning a gate voltage between 20V and −60V at a drain voltage of −60V. From the resultant voltage current curve, it was found that the transistor has a carrier mobility of 5.6 $cm^2$/Vs, a threshold voltage of −6V and an $I_{on}/I_{off}$ of $10^7$.

Example 2

An n-doped silicon wafer containing a $SiO_2$ thermal oxidation film with a thickness of 300 nm (surface resistance 0.02 Ω·cm or less) treated with hexamethyldisilazane was placed in a vacuum vapor deposition apparatus, which was evacuated until degree of vacuum in the apparatus reached $1.0\times10^{-3}$ Pa or less. In accordance with a resistance heating vapor deposition method, a compound of formula (10) was vapor-deposited onto the electrode to a thickness of 50 nm at a vapor deposition rate of 1 Å/sec at a substrate temperature of about 100° C. to form a semiconductor layer (2). Subsequently, to the substrate, a shadow mask for forming an electrode was attached. The resultant substrate was placed in a vacuum vapor deposition apparatus, which was evacuated until degree of vacuum in the apparatus reached $1.0\times10^{-4}$ Pa or less. By the resistance heating vapor deposition method, gold electrodes, which are a source electrode (1) and a drain electrode (3), were vapor-deposited to a thickness of 50 nm to obtain a TC (top contact) type field effect transistor (channel length 50 μm, channel width 2 mm) of the present invention.

Similarly to Example 1, in the field effect transistor of the Example, the thermal oxidation film of the n-doped silicon wafer has the function of an insulating layer (4) and the n-doped silicon wafer thus has the functions of a substrate (6) and a gate electrode (5) (see FIG. 1-B). The resultant field effect transistor was placed in a prober to measure a semiconductor property by a semiconductor parameter analyzer 4200SCS (manufactured by Keithley). To assess the semiconductor property, a drain current-gate voltage (transfer) characteristic was measured by scanning a gate voltage between 20V to −60V at a drain voltage of −30V. From the resultant voltage current curve, it was found that the transistor has a carrier mobility of 1.2 $cm^2$/Vs, a threshold voltage of −0.2V, a current value of 1.3 mA at a gate voltage of −30V, and an $I_{on}/I_{off}$ of $10^7$.

Example 3

After the field effect transistor formed in Example 2 was stored in the air for 71 days, the semiconductor property was measured in the same conditions as in Example 2. From the resultant voltage current curve, it was found that the transistor has a carrier mobility of 1.3 $cm^2$/Vs, a current value of 1.5 mA at a gate voltage of −30V, and an $I_{on}/I_{off}$ of $10^7$ after 71 days. The initial properties and performance were maintained even if the transistor was stored in the air.

Example 4

The field effect transistor formed in Example 2 was heated at 250° C. for 30 minutes and the semiconductor properties before and after the heating were measured in the same conditions as in Example 2. From the resultant voltage current curve, it was found that the transistor has a carrier mobility of 1.2 $cm^2$/Vs and a current value of 1.5 mA at a gate voltage of −30V after heating. After the transistor was exposed to high temperature, the high mobility and current value were maintained.

Comparative Example 1

A field effect transistor was formed in the same manner as in Example 2, except that a compound of formula (10) in Example 2 was replaced with compound (DNTT) described in Patent Literature 5 (Example 1):

[Formula 7]

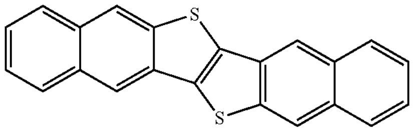

The semiconductor property was measured in the same conditions in Example 2. From the resultant voltage current curve, it was found that the transistor (containing comparative compound) has a carrier mobility of 0.42 $cm^2/Vs$, and a current value of 0.08 mA at a gate voltage of −30V. The property deteriorated as compared to Example 2.

Comparative Example 2

The field effect transistor formed in Comparative Example 1 was heated at 150° C. for 30 minutes, and the semiconductor properties before and after the heating were measured in the same conditions as in Example 2. From the resultant voltage current curve, it was found that the device has a carrier mobility of 0.25 $cm^2/Vs$ and a current value of 0.02 mA at a gate voltage of −30V after heating. It was found that the semiconductor property deteriorated by the effect of heat even in the temperature conditions lower by 100° C. than in Example 4.

As is apparent from Examples and Comparative Examples mentioned above, compounds represented by general formula (1) of the present invention have excellent properties as an organic thin-film transistor and an organic solar cell device and would be extremely useful compounds in terms of high general versatility as an organic electronics device.

REFERENCE SIGNS LIST

The same numerals are used to denote the same names in FIG. 1 to FIG. 2.

1 Source electrode

2 Semiconductor layer

3 Drain electrode

4 Insulating layer

5 Gate electrode

6 Substrate

7 Protective layer

The invention claimed is:

1. A heterocyclic compound represented by the general formula (1):

[Formula 1]

(1)

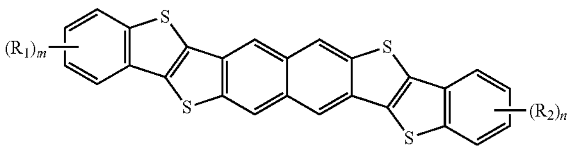

wherein $R_1$ and $R_2$ independently represent a hydrogen atom, an aryl group that may have a substituent or an alkyl group that may have a substituent; m and n independently represent an integer of 1 to 4; and when $R_1$ and $R_2$ are each two or more, one of $R_1$'s and one of $R_2$'s may be the same as or different from one another.

2. The heterocyclic compound according to claim 1, wherein $R_1$ and $R_2$ each are a hydrogen atom or an alkyl group that may have a substituent.

3. The heterocyclic compound according to claim 2, wherein $R_1$ and $R_2$ each are a hydrogen atom or a C1 to C3 lower alkyl group.

4. The heterocyclic compound according to claim 3, wherein $R_1$ and $R_2$ each are a hydrogen atom.

5. An organic semiconductor material containing the compound according to any one of claims 1 to 4.

6. A thin film containing the organic semiconductor material according to claim 5.

7. An organic electronics element comprising an organic semiconductor material according to claim 5.

8. The organic electronics element according to claim 7, wherein the organic electronics element is a thin-film transistor element, a photoelectric conversion element, an organic solar cell, an organic EL element, an organic light emitting transistor element or an organic semiconductor laser element.

9. The organic electronics element according to claim 8, wherein the organic electronics element is a thin-film transistor element, a photoelectric conversion element or an organic solar cell.

10. The organic electronics element according to claim 8, wherein the organic electronics element is a thin-film transistor element.

* * * * *